US009144395B2

(12) United States Patent
Sela et al.

(10) Patent No.: US 9,144,395 B2
(45) Date of Patent: Sep. 29, 2015

(54) GUIDEWIRE INTERCONNECTING APPARATUS

(71) Applicant: MediGuide, Ltd., Haifa (IL)

(72) Inventors: Ran Sela, Tel Aviv-Yafo (IL); Nimrod Meller, Kiryat Tivon (IL); Lior Sobe, Kadima (IL); Aharon Gildin, Haifa (IL); Gera Strommer, Haifa (IL); Uzi Eichler, Haifa (IL)

(73) Assignee: MediGuide, Ltd., Haifa (IL)

( * ) Notice: Subject to any disclaimer, the term of this patent is extended or adjusted under 35 U.S.C. 154(b) by 0 days.

(21) Appl. No.: 14/481,628

(22) Filed: Sep. 9, 2014

(65) Prior Publication Data

US 2014/0378869 A1 Dec. 25, 2014

Related U.S. Application Data

(63) Continuation of application No. 12/359,010, filed on Jan. 23, 2009, now Pat. No. 8,858,468.

(60) Provisional application No. 61/028,665, filed on Feb. 14, 2008, provisional application No. 61/023,007, filed on Jan. 23, 2008.

(51) Int. Cl.
*A61B 5/00* (2006.01)
*A61M 25/00* (2006.01)
*A61B 5/06* (2006.01)
(Continued)

(52) U.S. Cl.
CPC . *A61B 5/065* (2013.01); *A61B 5/06* (2013.01); *A61B 5/6851* (2013.01); *A61B 17/00234* (2013.01); *A61M 25/09* (2013.01); *A61M 25/0905* (2013.01); *A61B 2017/00292* (2013.01); *A61B 2017/00464* (2013.01); *A61B 2017/00469* (2013.01); *A61B 2017/00473* (2013.01); *A61B 2017/22042* (2013.01); *A61B 2019/5251* (2013.01); *A61M 2025/0002* (2013.01); *A61M 2025/0915* (2013.01); *A61M 2025/09083* (2013.01); *A61M 2025/09108* (2013.01); *A61M 2025/09133* (2013.01);
(Continued)

(58) Field of Classification Search
CPC .................. A61M 25/09; A61M 2025/09116; A61B 5/065
USPC ......... 600/433, 434, 585; 29/594; 604/164.13
See application file for complete search history.

(56) References Cited

U.S. PATENT DOCUMENTS 4,873,986 A * 10/1989 Wallace ........................ 600/483
5,105,818 A * 4/1992 Christian et al. .............. 600/463
(Continued)

FOREIGN PATENT DOCUMENTS

EP 0925803 6/1999
JP 07-255726 10/1995
(Continued)

*Primary Examiner* — Brian Szmal
(74) *Attorney, Agent, or Firm* — Dykema Gossett PLLC

(57) ABSTRACT

A male coupler for a guidewire, the guidewire having a hollow walled tube, the male coupler comprising a connector section, coupled with the guidewire, a portion of the connector section having a diameter smaller than the diameter of the hollow tube, at least one conducting ring coupled with the connector section where the diameter of the connector section is smaller the diameter of the guidewire, wherein the diameter of connector section and the at least one conducting ring substantially equals the diameter of the guidewire.

13 Claims, 15 Drawing Sheets

(51) Int. Cl.
  *A61M 25/09* (2006.01)
  *A61B 17/00* (2006.01)
  *A61B 17/22* (2006.01)
  *A61B 19/00* (2006.01)

(52) U.S. Cl.
  CPC ............... *A61M 2025/09175* (2013.01); *A61M 2205/3515* (2013.01); *H01R 2201/12* (2013.01); *Y10T 29/49002* (2015.01)

(56) References Cited

U.S. PATENT DOCUMENTS

| | | | | |
|---|---|---|---|---|
| 5,178,159 A | * | 1/1993 | Christian | 600/585 |
| 5,240,437 A | * | 8/1993 | Christian | 439/668 |
| 5,630,426 A | * | 5/1997 | Eggers et al. | 600/547 |
| RE35,648 E | | 11/1997 | Tenerz et al. | |
| 5,938,624 A | * | 8/1999 | Akerfeldt et al. | 600/585 |
| 6,090,052 A | * | 7/2000 | Akerfeldt et al. | 600/585 |
| 6,196,980 B1 | | 3/2001 | Akerfeldt et al. | |
| 6,210,339 B1 | * | 4/2001 | Kiepen et al. | 600/486 |
| 6,428,336 B1 | * | 8/2002 | Akerfeldt | 439/263 |
| 6,428,489 B1 | * | 8/2002 | Jacobsen et al. | 600/585 |
| 2005/0091833 A1 | * | 5/2005 | Kiepen et al. | 29/594 |

FOREIGN PATENT DOCUMENTS

| | | |
|---|---|---|
| WO | 98/24664 | 6/1998 |
| WO | 99/13532 | 3/1999 |
| WO | 00/51489 | 9/2000 |

\* cited by examiner

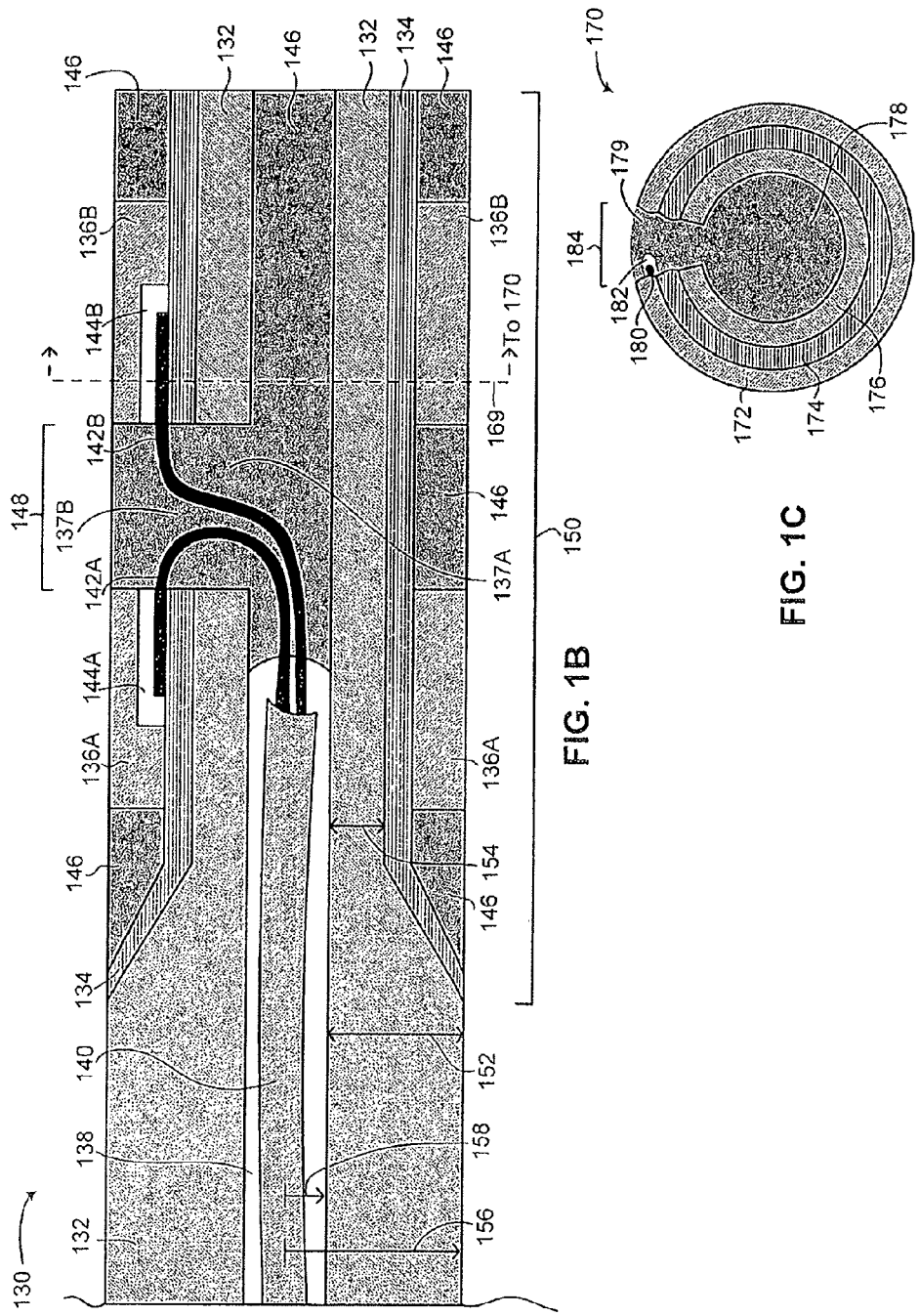

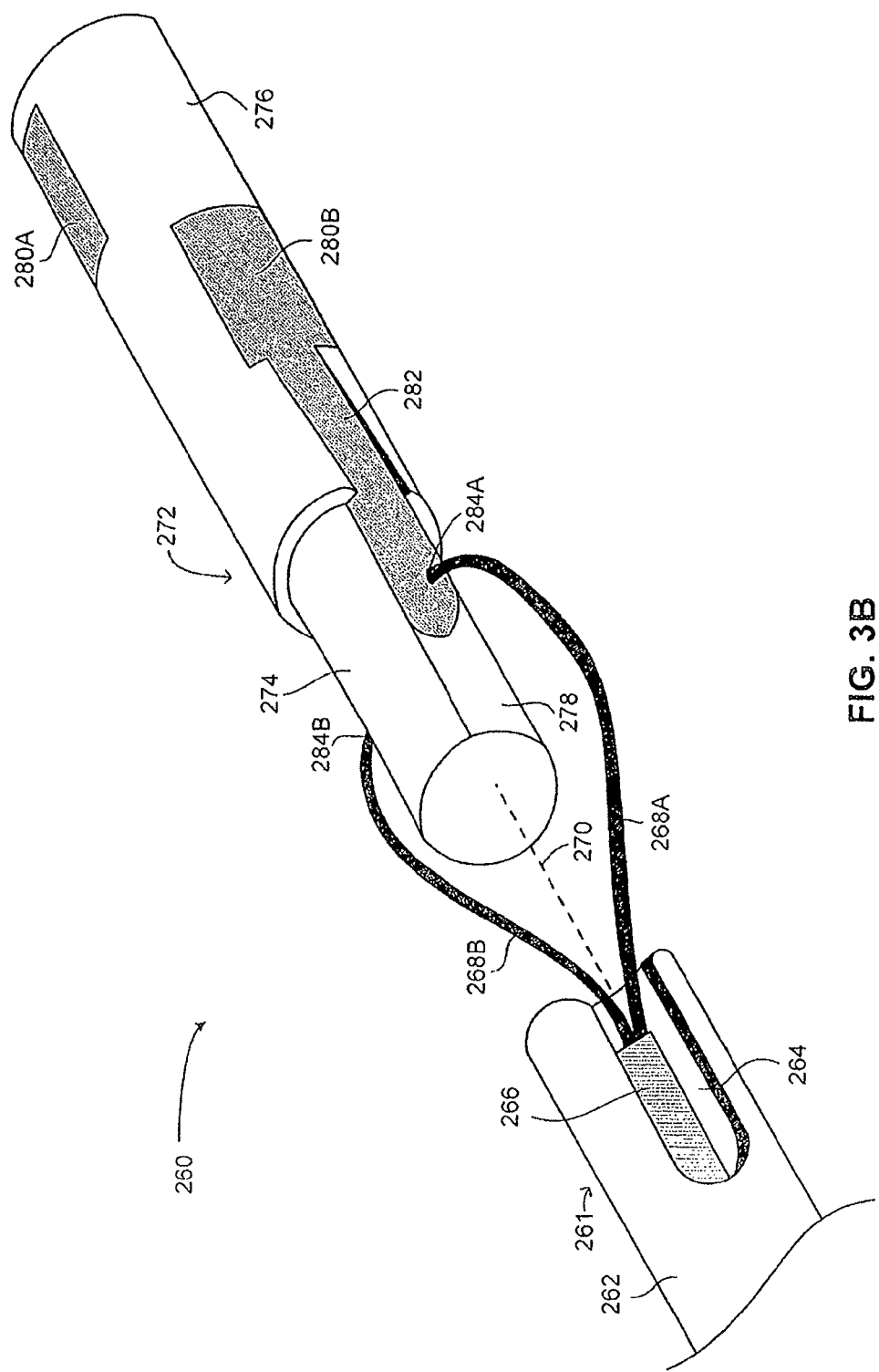

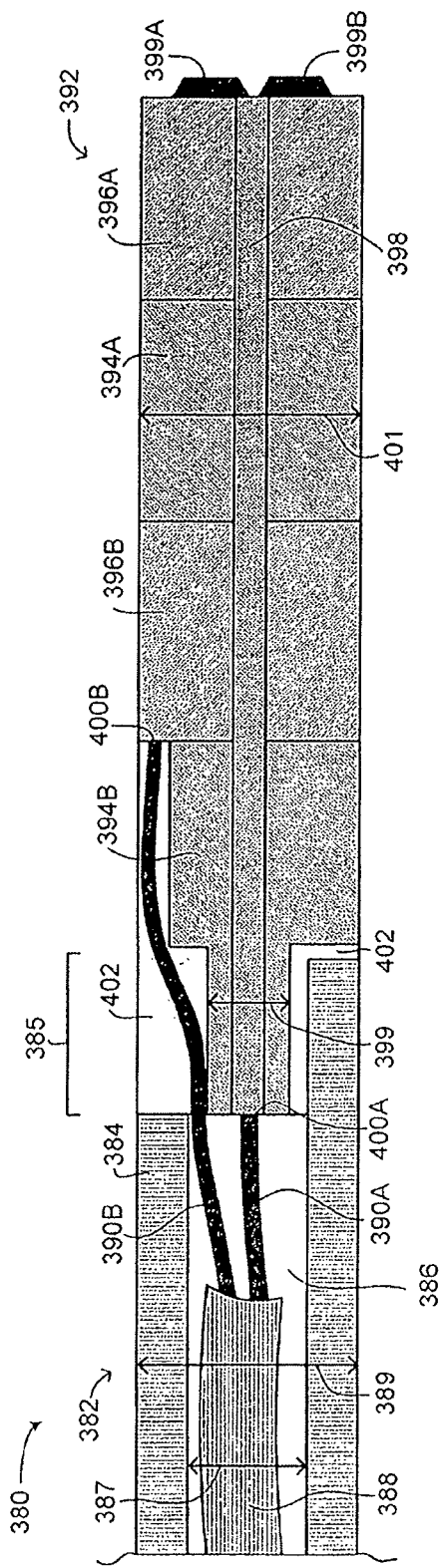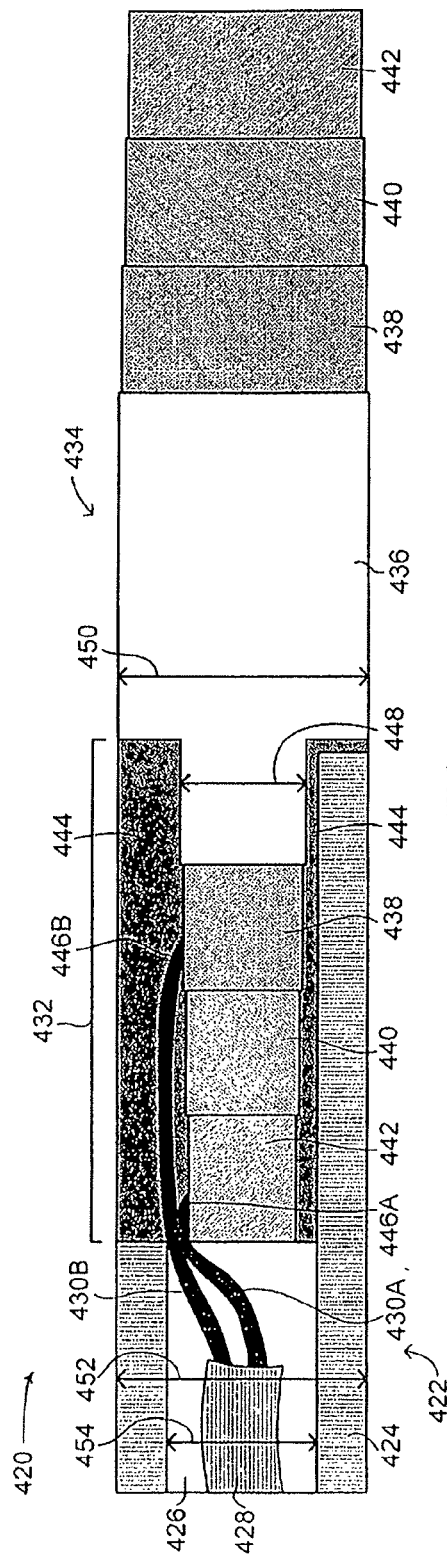

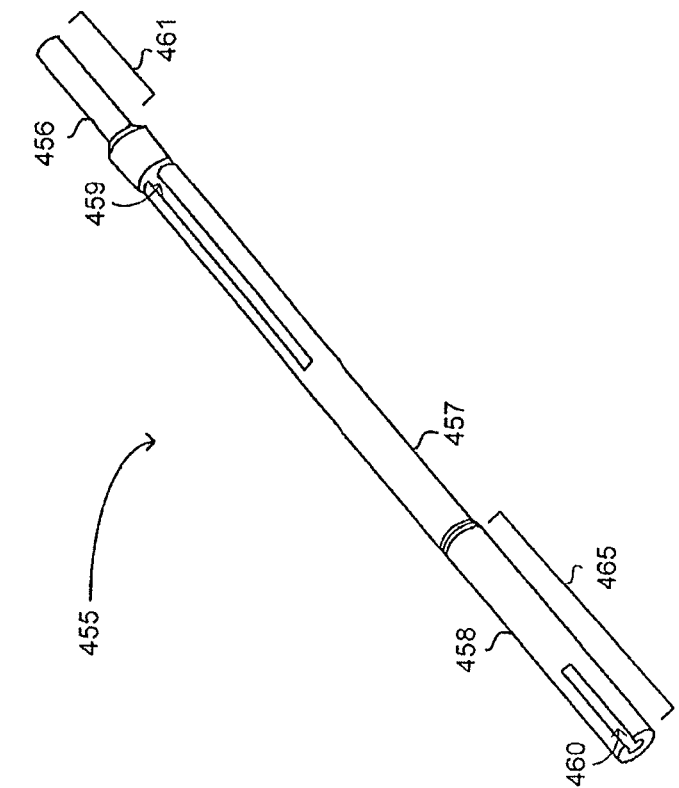
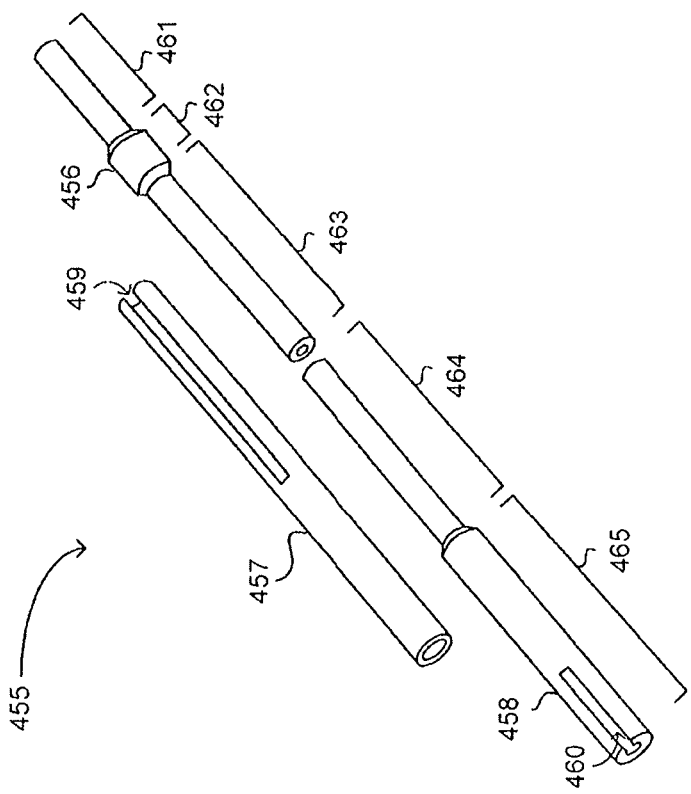

GUIDEWIRE INTERCONNECTING APPARATUS

CROSS-REFERENCE TO RELATED APPLICATIONS

This application is a continuation of U.S. application Ser. No. 12/359,010, filed 23 Jan. 2009, now pending ("the '010 application"), which claims the benefit of U.S. provisional application No. 61/023,007, filed 23 Jan. 2008 ("the '007 application") and U.S. provisional application No. 61/028, 665, filed 14 Feb. 2008 ("the '665 application"). The '010 application, the '007 application, and the '665 application are all hereby incorporated by reference as though fully set forth herein.

FIELD OF THE DISCLOSED TECHNIQUE

The disclosed technique relates to guidewires in general, and to methods and systems for interconnecting a guidewire which includes electronic elements, in particular.

BACKGROUND OF THE DISCLOSED TECHNIQUE

Guidewires are employed in noninvasive operations, for example, to enable a physician to navigate to a desired location within the lumen of the body of a patient, and then insert a catheter to the desired location, with the aid of the guidewire. Such guidewires are known in the art. One type of guidewire includes a sensor positioned in its tip. The sensor is connected with a pair of wires which pass along the guidewire. The wires are connected to a male connector coupled with the guidewire. The male connector connects with a female connector. The female connector is connected to medical equipment.

U.S. Pat. No. 6,090,052 to Akerfeldt et al., entitled "Guide Wire Having a Male Connector" is directed towards a guidewire which includes a corewire. Electrical leads are connected to the sensor at the distal end of the guidewire. The electrical leads extend along the length of the corewire over a thin flexible sheet partially wrapped around the corewire. The flexible sheet has a wider portion at the proximal end of the guidewire. The electrical leads connect to conductive strips formed on the wider portion of the flexible sheet. The electrical leads and the conductive strips form the general shape of "a flag pole with a flag." The wide portion of the flexible sheet, with the conductive strips are wrapped around the proximal end of the corewire, thereby forming cylindrical shaped contacts.

U.S. Pat. No. 6,428,336, to Akerfeldt, entitled "Female so Connector" is directed towards a female connector for a guidewire including an insulating hollow housing containing three hollow contact members having the shape of a cylinder. The housing includes an opening for inserting a male connector of a guidewire and three contact seats. The housing further includes means for securing a male connector of a guidewire in the female connector. The hollow contact members are disposed on the contact seats. An interface cable is connected to the contact members. A male connector is inserted into the opening of the housing and is secured in place by the means for securing. The contact members provide electrical contact with the male connector.

SUMMARY OF THE PRESENT DISCLOSED TECHNIQUE

It is an object of the disclosed technique to provide a novel male and female couplers for a guidewire.

In accordance with the disclosed technique, there is thus provided a male coupler for a guidewire. The guidewire has a hollow walled tube. The male coupler includes a connector section and at least one conducting ring. A portion of the connector section has a diameter smaller than the diameter of the hollow tube. The connector section is coupled with the guidewire. The at least one conducting ring is coupled with the connector section where the diameter of said connector section is smaller than the diameter of the guidewire. The diameter of the connector section and the at least one conducting ring substantially equals the diameter of the guidewire.

In accordance with another aspect of the disclosed technique, there is thus provided a female coupler for a guidewire. The female coupler includes a disposable part and a non-disposable part. The disposable part includes a disposable tubular body, at least one conducting spring, a sheath and a collet. The disposable tubular body has an open end and a closed end. The at least one conducting spring is coupled with the disposable tubular body such that each of the at least one conducting spring has a portion thereof in contact with the inner wall of the disposable tubular body and a portion in contact with the outer wall of the disposable tubular body. The sheath is coupled with said disposable tubular body at the open end of the disposable tubular body. The sheath extends towards the closed end of the disposable tubular body. The collet is coupled with the open end of said disposable tubular body for securing a male coupler within the disposable tubular body. The non-disposable part includes a non-disposable tubular body and at least one contact. The at least one contact is coupled with the non-disposable tubular body such that the circumference of the at least one contact encircles a portion of the circumference of the inner wall of the non-disposable tubular body. The disposable part is insertable into the non-disposable part. The at least one conducting spring is in electrical contact with the at least one contact when the disposable part is fully inserted into said non-disposable part.

In accordance with a further aspect of the disclosed technique, there is thus provided a guidewire having a hollow walled tube. The guidewire includes a male connector and a female connector. The male coupler includes a connector section and at least one conducting ring. A portion of the connector section has a diameter smaller than the diameter of the hollow tube. The connector section is coupled with the guidewire. The at least one conducting ring is coupled with the connector section where the diameter of said connector section is smaller than the diameter of the guidewire. The female connector includes a disposable part and a non-disposable part. The disposable part includes a disposable tubular body, at least one conducting spring, a sheath and a collet. The disposable tubular body has an open end and a closed end. The at least one conducting spring is coupled with the disposable tubular body such that each of the at least one conducting spring has a portion thereof in contact with the inner wall of the disposable tubular body and a portion in contact with the outer wall of the disposable tubular body. The sheath is coupled with said disposable tubular body at the open end of the disposable tubular body. The sheath extends towards the closed end of the disposable tubular body. The collet is coupled with the open end of said disposable tubular body for securing a male coupler within the disposable tubular body. The non-disposable part includes a non-disposable tubular body and at least one contact. The at least one contact is coupled with the non-disposable tubular body such that the circumference of the at least one contact encircles a portion of the circumference of the inner wall of the non-disposable tubular body. The diameter of the connector section and the at least one conducting ring substantially equals the diameter of the guidewire. The disposable part is insertable into the non-disposable part. The at least one conducting spring is in electrical contact with the at least one contact when the disposable part is fully inserted into said non-disposable part. The male coupler is insertable into the disposable part of said female coupler. When the male coupler is inserted into the female coupler the at least one conducting ring is in electrical contact with a respective one of said at least one conducting springs.

BRIEF DESCRIPTION OF THE DRAWINGS

The disclosed technique will be understood and appreciated more fully from the following detailed description taken in conjunction with the drawings in which:

FIG. 1B is a cross-section illustration of the guidewire of FIG. 1A along a plane parallel to the length of the guidewire, constructed and operative in accordance with another embodiment of the disclosed technique;

FIG. 1C is a cross-section illustration of the guidewire of FIG. 1B along a plane perpendicular to the length of the guidewire, constructed and operative in accordance with a further embodiment of the disclosed technique;

FIG. 3B is another perspective exploded illustration of the guidewire insert of FIG. 2 coupled with a guidewire, constructed and operative in accordance with another embodiment of the disclosed technique;

FIG. 4B is a cross-section illustration of the guidewire insert of FIG. 4A, coupled with a guidewire, constructed and operative in accordance with a further embodiment of the disclosed technique;

FIG. 5 is a cross-section illustration of a further guidewire insert, coupled with a guidewire, constructed and operative in accordance with another embodiment of the disclosed technique;

FIG. 6A, is a schematic perspective exploded illustrations of the guidewire male coupler, constructed and operative in accordance with a further embodiment of the disclosed technique;

FIG. 6B, is a schematic perspective illustrations of the guidewire male coupler assembled, constructed and operative in accordance with a further embodiment of the disclosed technique;

DETAILED DESCRIPTION OF THE EMBODIMENTS

Figure 1A:
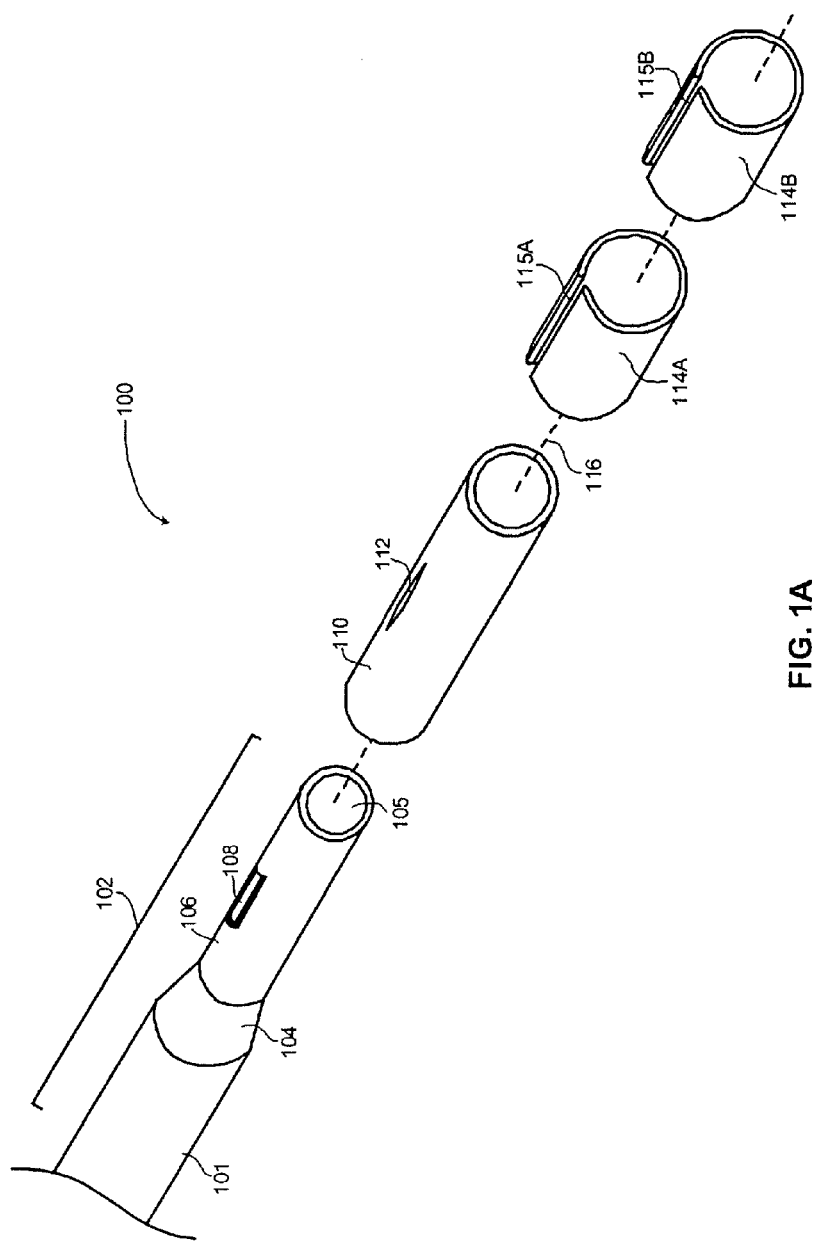
FIG. 1A is a perspective exploded illustration of a guidewire including a male coupler, constructed and operative in accordance with an embodiment of the disclosed technique.

The disclosed technique overcomes the disadvantages of the prior art by providing a novel apparatus and method for interconnecting a guidewire, which includes electronic elements, to an external system. The external system enables electrical signals to be received from the electronic elements of the guidewire. The disclosed technique enables the guidewire to be coupled and decoupled to the external system a plurality of times in a rapid and simple manner. The apparatus of the disclosed technique is designed such that it has the same diameter as the guidewire, thereby enabling catheters and other like devices to be easily positioned on and removed from the guidewire. In addition, the apparatus of the disclosed technique has a strength and stability similar to that of the guidewire's body, thereby enabling the apparatus of the disclosed technique to withstand tensile, compressive and rotation forces similar to those that the body of the guidewire can withstand.

It is noted that, as an example, the disclosed technique is described herein with reference to guidewires. However, the disclosed technique may be used with other similar devices, such as stylets, catheters bearing balloons, stents or other devices for performing interventional or diagnostic functions, all of which can be used in medical applications. Also, throughout the description, the terms "couple," "connect" and "attach" are used interchangeably, and the terms "decouple," "disconnect" and "detach" are also used interchangeably. In general, the disclosed technique relates to apparatuses and methods for interconnecting guidewires, which include electronic elements, to an external system. Such electronic elements may include various types of sensors, such as heat sensors, pressure sensors, magnetic position sensors and the like. In general, such sensors are located in a portion of the body of a guidewire and include electrical wires. Such wires provide electric signals generated by the sensors to an external system and also provide electric signals generated by the external system to the sensors. The external system may be a power supply, an oscilloscope, a computer, medical equipment and the like.

In various applications, guidewires are inserted into different types of bodies. For example, in medical applications, guidewires may be inserted into blood vessels, arteries, internal organs and the like of a patient. Such guidewires, which have electronic elements coupled to an external system, need to be decoupled from the external system to enable a user, such as a physician, to slip a device, such as a catheter, over the guidewire. Once the device has been slipped over the guidewire, the guidewire needs to be re-coupled with the external system to enable signals to be received from the electronic elements. Also, such guidewires are usually disposable one-time use devices which need to be decoupled from the external system after each use and thrown away. In certain medical applications, such guidewires need to be decoupled from the external system to be cleaned and sterilized between uses. As described below, the disclosed technique provides for a system whereby the electronic elements of the guidewire are coupled with an interconnecting apparatus. The interconnecting apparatus is physically coupled with the guidewire. The interconnecting apparatus includes contact surfaces which can be coupled with an external system for providing and transferring electrical signals. According to the disclosed technique, the external system is provided with a receiving apparatus for receiving the interconnecting apparatus which is physically coupled with the guidewire. In general, the interconnecting apparatus can be referred to as an interconnect, and the two terms "interconnecting apparatus" and "interconnect" are used interchangeably throughout the description. As a convention used in the description, the section of the disclosed technique which is physically coupled with the guidewire is referred to as a male coupler, or a male connector, whereas the section of the disclosed technique which is provided with the external system for receiving the male coupler is referred to as a female coupler, or a female connector. In other words, the disclosed technique relates to an interconnect, which includes two sections, a male coupler and a female coupler. As described below, the male coupler is physically coupled with the guidewire and the female coupler is physically coupled with the external system. The male coupler can be rapidly and simply coupled with the female coupler, thereby coupling the electronic elements of the guidewire to the external system.

Reference is now made to FIG. 1A, which is a perspective exploded illustration of a guidewire including a male coupler, generally referenced 100, constructed and operative in accordance with an embodiment of the disclosed technique. In guidewire 100, the male coupler, as described below, is integrated as a part of the guidewire. Guidewire 100 includes a proximal section 102. Proximal section 102 represents the end section of guidewire 100 which is coupled with an external system (not shown) and includes a regular section 101, a transition section 104 and a reduced diameter section 106. A distal section (not shown) of guidewire 100 represents the other end section of guidewire 100 which is usually inserted into a body. Guidewire 100 is constructed of a walled tube which is hollow. In one embodiment of the disclosed technique, the walled tube is a thick walled tube. In general, throughout the description, the term hollow walled tube is used to designate a hollow walled tube of a predetermined thickness and includes hollow walled tubes which are thick and thin. The hollow 105 of guidewire 100 can be referred to as a cavity or a lumen. As shown in FIG. 1B, the walled tube includes an inner diameter and an outer diameter (not shown in FIG. 1A). Regular section 101 represents the size, and in particular the diameter, of the walled tube of the guidewire over a majority of the length of the guidewire. Transition section 104 represents a section of proximal section 102 wherein the outer diameter of the walled tube is gradually reduced in size to a predetermined reduced size. Reduced diameter section 106 represents the end section of proximal section 102 wherein the outer diameter of the walled tube is maintained constant at the predetermined reduced size. Transition section 104 and reduced diameter section 106 can be formed by numerous techniques known in the art such as drawing both sections over a mandrel, machining the sections, grinding the sections, using a centerless grinding process, using a cold working process and the like.

In another embodiment of the disclosed technique, transition section 104 and reduced diameter section 106 are replaced by a second walled tube (not shown). This second walled tube would have an outer diameter substantially similar to the inner diameter of regular section 101, and would have a length substantially similar to the combined length of transition section 104 and reduced diameter section 106. In this embodiment, the second walled tube is inserted into regular section 101 and is either welded or bonded to regular section 101. In this embodiment, the diameters of the walled tube and the second walled tube could be on the order of hundreds of micrometers (i.e., tenths of a millimeter). For example, the outer diameter of regular section 101 could be 0.35 millimeters, with an inner diameter of 0.18 millimeters. The outer diameter of the second walled tube could be 0.18 millimeters, with an inner diameter of 0.09 millimeters.

In reduced diameter section 106, an aperture 108 is formed, exposing lumen 105 of guidewire 100. In the embodiment just described which includes a second walled tube, aperture 108 would be formed on the second walled tube. Aperture 108 can be formed by using techniques known in the art such as machining, micro-machining, cutting, laser cutting, electrical discharge machining (EDM), chemical etching and the like. Aperture 108 is formed to be large enough to thread electrical elements, such as electrical wires (not shown), in guidewire 100 there through. As mentioned above, FIG. 1A represents a perspective exploded illustration wherein the various elements of guidewire 100 are separated but kept in the general order in which they are physically assembled. The separated elements are positioned along a respective centerline, shown in FIG. 1A as a dotted line 116. The assembled elements are shown in detail in FIGS. 1B and 1C. Over transition section 104 and reduced diameter section 106, a cover section 110 is positioned. Cover section 110, like guidewire 100, can be constructed from a walled tube, which would have an inner diameter and an outer diameter (both not shown). Cover section 110 can also be a shrinkable polymer tube, a coating, a polymeric ceramic or a non-conducting ceramic. Cover section 110 is generally made of an electrically insulating material such as polyester (a polymeric heat shrink), Teflon® (a polymeric coating) or alumina (a coating). Cover section 110 may be a polymer coating, a non-conducting ceramic, a heat shrink tube, a shrinkable polymer tube and the like. The length of cover section 110 is substantially similar to the combined lengths of transition section 104 and reduced diameter section 106. The inner diameter of cover section 110 is substantially the same size of the outer diameter of reduced diameter section 106. The outer diameter of cover section 110 is smaller than the outer diameter of regular section 101. Cover section 110 includes an aperture 112. Aperture 112 is substantially similar in size to aperture 108. If cover section 110 is a coating, then aperture 112 is substantially a slit, similar in length to aperture 108. Aperture 112 is positioned on cover section 110 such that when cover section 110 is placed around transition section 104 and reduced diameter section 106, aperture 112 and aperture 108 are aligned.

Once cover section 110 has been positioned around transition section 104 and reduced diameter section 106, rings 114A and 114B are positioned over cover section 110. In general, rings 114A and 114B are tubes which have an inner diameter and an outer diameter (not shown). The outer diameter of the rings is substantially similar to the outer diameter of regular section 101. The inner diameter of the rings is substantially similar to the outer diameter of cover section 110. In one embodiment, rings 114A and 114B can be made from an electrically conductive material. In another embodiment, rings 114A and 114B are coated, or plated, with an electrically conductive material. In general, the material from which rings 114A and 114B is either made from, coated or plated, is biocompatible. In the embodiment shown in FIG. 1A, two rings are positioned over cover section 110. In another embodiment, a plurality of rings is positioned over cover section 110. In general, the amount of rings included in guidewire 100 is determined by the number of electrical signal paths required for the electrical elements inside guidewire 100. For example, if guidewire 100 includes a magnetic position sensor (not shown) and a temperature sensor (not shown), then guidewire 100 requires four electrical signal paths (i.e. four electrical wires), two for the magnetic position sensor and two for the temperature sensor. For each electrical wire placed in lumen 105, a respective ring is positioned over cover section 110. In one embodiment, rings 114A and 114B are completely closed (not shown). In another embodiment, as shown in FIG. 1A, rings 114A and 114B are open, having openings 115A and 115B. Rings 114A and 114B can be positioned over cover section 110 by sliding the rings over the cover section. Rings 114A and 114B can also be crimped over cover section 110. Rings 114A and 114B are placed over cover section 110 such that they do not cover aperture 112 and such that they do not make contact with each other.

As described below in FIGS. 1B and 1C, rings 114A and 114B are conducting surfaces to which electrical elements in guidewire 100, such as electrical wires, are coupled to. Rings 114A and 114B can then be coupled with conducting surfaces on an external system (not shown), in particular to a female coupler (not shown) coupled with the external system. In this respect, rings 114A and 114B, cover section 110, transition section 104 and reduced diameter section 106 represent an embodiment of the male coupler of the disclosed technique. The male coupler shown in FIGS. 1A, 1B and 1C is an integrated part of guidewire 100 as the conducting surfaces, rings 114A and 114B, are positioned over the proximal section of guidewire 100. As shown in the embodiments in FIGS. 2-5, the male coupler in these embodiments is not an integrated part of the guidewire but is rather an element upon which conducting surfaces are formed and which is then coupled with the proximal section of the guidewire.

Reference is now made to FIG. 1B, which is a cross-section illustration of the guidewire of FIG. 1A along a plane parallel to the length of the guidewire, generally referenced 130, constructed and operative in accordance with another embodiment of the disclosed technique. Guidewire 130 includes an integrated male coupler, as described below. In FIG. 1B, the separated parts of FIG. 1A, such as cover section 110 (FIG. 1A) and rings 114A and 114B (both in FIG. 1A) have been positioned in their respective order over guidewire 130. As mentioned above, guidewire 130 is constructed from a walled hollow tube. Guidewire 130 includes a walled section 132, a lumen 138, a pair of electrical wires 140, a cover section 134 and rings 136A and 136B. Pair of electrical wires 140 includes a first wire 142A and a second wire 142B. Walled section 132 is substantially similar to regular section 101 (FIG. 1A), cover section 134 is substantially similar to cover section 110 (FIG. 1A) and rings 136A and 136B are substantially similar to rings 114A and 114B (both in FIG. 1A). The section of guidewire 130 which is shown in FIG. 1B represents the proximal section of the guidewire. Over a majority of the length of guidewire 130, walled section 132 has a thickness shown by an arrow 152. As mentioned in FIG. 1A, at the end of the proximal section of guidewire 130, shown in FIG. 1B as a male coupler section 150, the thickness of walled section 132 is reduced in size. As shown in FIG. 1B, the thickness of walled section 132, as shown by arrow 152, is reduced to a predetermined thickness, as shown by an arrow 154. The thickness represented by arrow 152 is reduced gradually to the thickness represented by arrow 154. It is noted that in reducing the thickness of walled section 132, the thickness of lumen 138 is not altered and remains constant along the entire length of guidewire 130. In another embodiment, the thickness of walled section 132 is reduced in size by drawing walled section 132 through a die. In this embodiment, both the outer diameter of guidewire 130, as denoted by an arrow 156, and the inner diameter of guidewire 130, as denoted by an arrow 158 are reduced in size. As such, the thickness of lumen 138 is also altered and is not constant along the entire length of guidewire 130.

Guidewire 130 also includes an aperture, delineated by a bracket 148. An aperture 137A opened up in walled section 132 and an aperture 137B opened up in cover section 134 are substantially similar in size and are aligned. The aperture delineated by bracket 148 is large enough such that first wire 142A and second wire 142B can be threaded there through. First wire 142A is coupled with ring 136A and second wire 142B is coupled with ring 136B. In general, each wire in lumen 138 is coupled in male coupler section 150 to a respective ring. As mentioned in FIG. 1A, guidewire 130 is not limited to including only two wires but can include a plurality of wires. Therefore, for each wire in lumen 138, a respective ring is positioned around cover section 134. As can be seen in FIG. 1B, rings 136A and 136B are positioned such that they do not cover the aperture delineated by bracket 148 and such that they do not make contact with each other. First wire 142A and second wire 142B are coupled respectively to rings 136A and 136B by dabs of conducting glue 144A and 144B. The first and second wires can be coupled with the rings by welding, soldering, brazing or bonding with a conductive bonding agent or glue. In one embodiment, the wires are first positioned on cover section 134 and then rings 136A and 136B are crimped over the wires, thereby forming a strong conductive path between the wires and the rings. In another embodiment, as shown in FIG. 1B, and more clearly in FIG. 1C, the rings are first positioned and then the wires are coupled to the rings as mentioned using, for example, a conducting glue. It is noted that walled section 132 can serve as a ground contact for electrical elements in lumen 138, such as pair of electrical wires 140. Once the wires have been coupled to the rings, the spaces between rings 136A and 136B as well as the aperture delineated by bracket 148 are filled with an insulating polymer 146. The end part of lumen 138 may also be filled with insulating polymer 146 to seal the lumen and to rigidly fix first wire 142A and second wire 142B. Insulating polymer 146 can also be an insulating bond or an insulating glue. Insulating polymer 146 is finally cured and smoothed, thus forming male coupler section 150 with a diameter substantially similar to the diameter of the rest of guidewire 130.

In general, rings 136A and 136 are open, as shown in FIG. 1A as rings 114A and 114B, to enable first wire 142A and second wire 142B to be coupled to the rings whereby a large conducting surface is provided for the coupling. Also, if rings 136A and 136B are open, then induced currents due to magnetic fields in pair of electrical wires 140 may be reduced. This is significant in an embodiment where guidewire 130 includes an electrical element which has a magnetic nature, such as a magnetic positioning sensor, since reduced induced currents is related to a reduction in noise in a signal received by an external system (not shown) coupled with rings 136A and 136B. As shown in FIG. 1B, a dotted line 169 shows a section of guidewire 130 which is shown in cross-section, in a plane perpendicular to the length of guidewire 130, in FIG. 1C.

Reference is now made to FIG. 1C, which is a cross-section illustration of the guidewire of FIG. 1B along a plane perpendicular to the length of the guidewire, generally referenced 170, constructed and operative in accordance with a further embodiment of the disclosed technique. Guidewire 170 is shown in cross-section in a male coupler section. Guidewire 170 includes a walled tube 176, a cover section 174, a ring 172 and a lumen 178. Guidewire 170 also includes an aperture 184. As can be seen, aperture 184 is aligned over the openings in walled tube 176, cover section 174 and ring 172. In this section of guidewire 170, ring 172 forms the outer layer, with cover section 174 being placed within ring 172 and walled tube 176 being placed within cover section 174. Lumen 178 and aperture 184 are filled with an insulating bond 179, which is cured and smoothed. In FIG. 1C, a wire 180 is coupled with ring 172 by a dab of conducting glue 182. In this embodiment, ring 172 is not crimped on top of wire 180, rather wire 180 is coupled with a face of ring 172 using dab of conducting glue 182.

Figure 2:
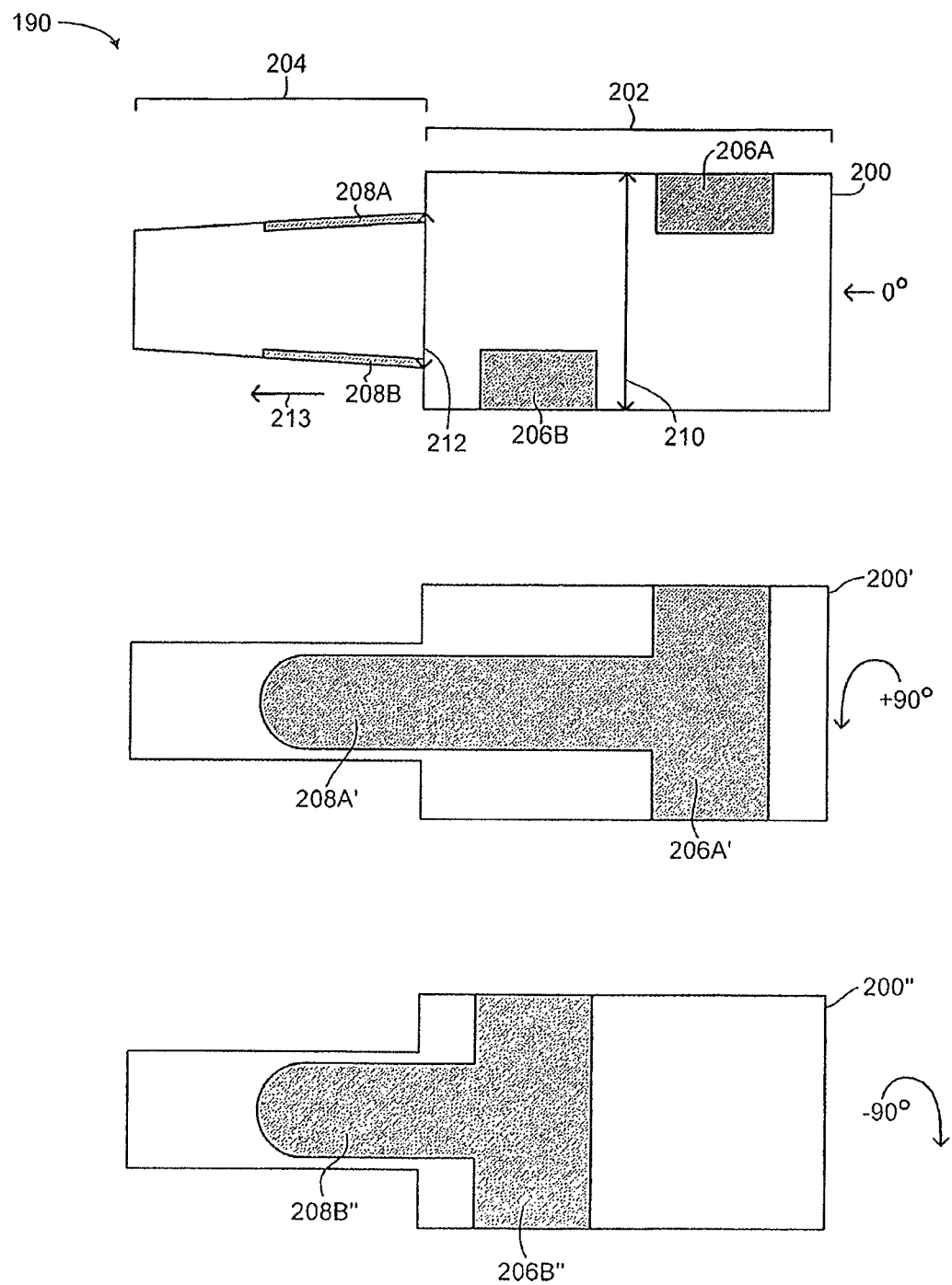
FIG. 2 is an orthographic illustration of a guidewire insert, constructed and operative in accordance with another embodiment of the disclosed technique.

Reference is now made to FIG. 2, which is an orthographic illustration of a guidewire insert, generally referenced 190, constructed and operative in accordance with another embodiment of the disclosed technique. As shown below in FIGS. 3A-3C, guidewire insert 190 is coupled with a guidewire (not shown) and in particular, is coupled with electrical elements in the guidewire, such as electrical wires. In FIG. 2, guidewire insert 190 is shown in three different orthographic projections. A guidewire insert 200 shows guidewire insert 190 from a side view, conventionally described as being at 0 degrees of rotation. A guidewire insert 200' shows guidewire insert 190 from a side view, at 90 degrees of rotation in a positive direction, which is the same as viewing guidewire insert 200 from a top view. A guidewire insert 200" shows guidewire insert 190 from a side view, at 90 degrees of rotation in a negative direction, which is the same as viewing guidewire insert 200 from a bottom view.

Guidewire insert 200 is constructed from a molded polymer. Guidewire insert 200 has a general cylindrical shape, shown in more detail in FIGS. 3A-3C, having a larger diameter section 202 and a smaller diameter section 204. Larger diameter section 202 has a diameter shown as an arrow 210, and smaller diameter section 204 has a diameter shown as an arrow 212. In guidewire 200, smaller diameter section 204 slightly tapers in the direction of an arrow 213, whereas in guidewire inserts 200' and 200", the smaller diameter section does not taper. Diameter 210 is substantially similar to the outer diameter of a guidewire (not shown) to which guidewire insert 200 is coupled with. Diameter 212 is substantially similar to the inner diameter of a guidewire (not shown) to which guidewire insert 200 is coupled with. In general, larger diameter section 202 and smaller diameter section 204 may have lengths which are on the order of tens of millimeters. For example, both larger diameter section 202 and smaller diameter section 204 may measure 10 millimeters.

In this embodiment, guidewire insert 200 is molded from a specially formulated resin, which when exposed to a specific type of laser energy becomes active. In the molded state, the resin is not platable, whereas in an activated state, the resin is platable. In general, plating refers to a surface-covering technique wherein a substance is deposited onto a surface. In guidewire insert 200, the resin which the guidewire insert is formed from is generally insulating in nature. Once the general shape of guidewire insert 200 has been formed, certain parts of the surface of the guidewire insert are activated by exposing those parts to a particular type of laser energy. Afterwards, the entire surface of guidewire insert 200 is plated with a conducting metal, such as with copper, nickel or gold. In one embodiment of the disclosed technique, the entire surface of guidewire insert 200 is first plated with a layer of copper, then with a layer of nickel and finally with a layer of gold. In general, the resin and the conducting metal surface are biocompatible. Due to the nature of the resin, only those parts of the surface of guidewire insert 200 which were activated are plated with the conducting metal, thereby forming a conducting layer on certain parts of the surface of guidewire insert 200. In general, this technique is referred to in the art as laser direct structuring (LDS).

As shown in guidewire insert 200, two partial rings 206A and 206B are activated and plated as well as two paths 208A and 208B. In other words, the surfaces delineated in guidewire insert 200 as partial rings 206A and 206B and paths 208A and 208B are conducting surfaces, whereas all other parts of the surface of guidewire insert 200 are insulating surfaces. Regarding their measurements, for example, each partial ring could measure between 3-5 millimeters along the axis of guidewire 200 (in the direction of arrow 213) with a spacing of between 1-3 millimeters between the two rings. Path 208A is coupled with partial ring 206A (not shown) and path 208B is coupled with partial ring 206B (not shown). Path 208A and partial ring 206A do not make contact with path 208B and partial ring 206B. It is noted that in another embodiment of the disclosed technique, partial ring 206A can be a full ring (not shown). In other words, in this embodiment a full ring conducting surface is formed in the position of partial ring 206A. In general, partial rings are formed so as to reduce induced electrical currents, which, as explained above, reduces noise in signals which are transferred when electrical elements used in the guidewire (not shown) which guidewire insert 190 is coupled with are magnetic in nature. As can be seen in guidewire insert 200', a partial ring 206A' is coupled with a path 208A' where both partial ring 206A' and path 208A' are conducting surfaces. In guidewire insert 200", a partial ring 206B" is coupled with a path 208B" where both partial ring 206B" and path 208B" are conducting surfaces.

Figure 3A:
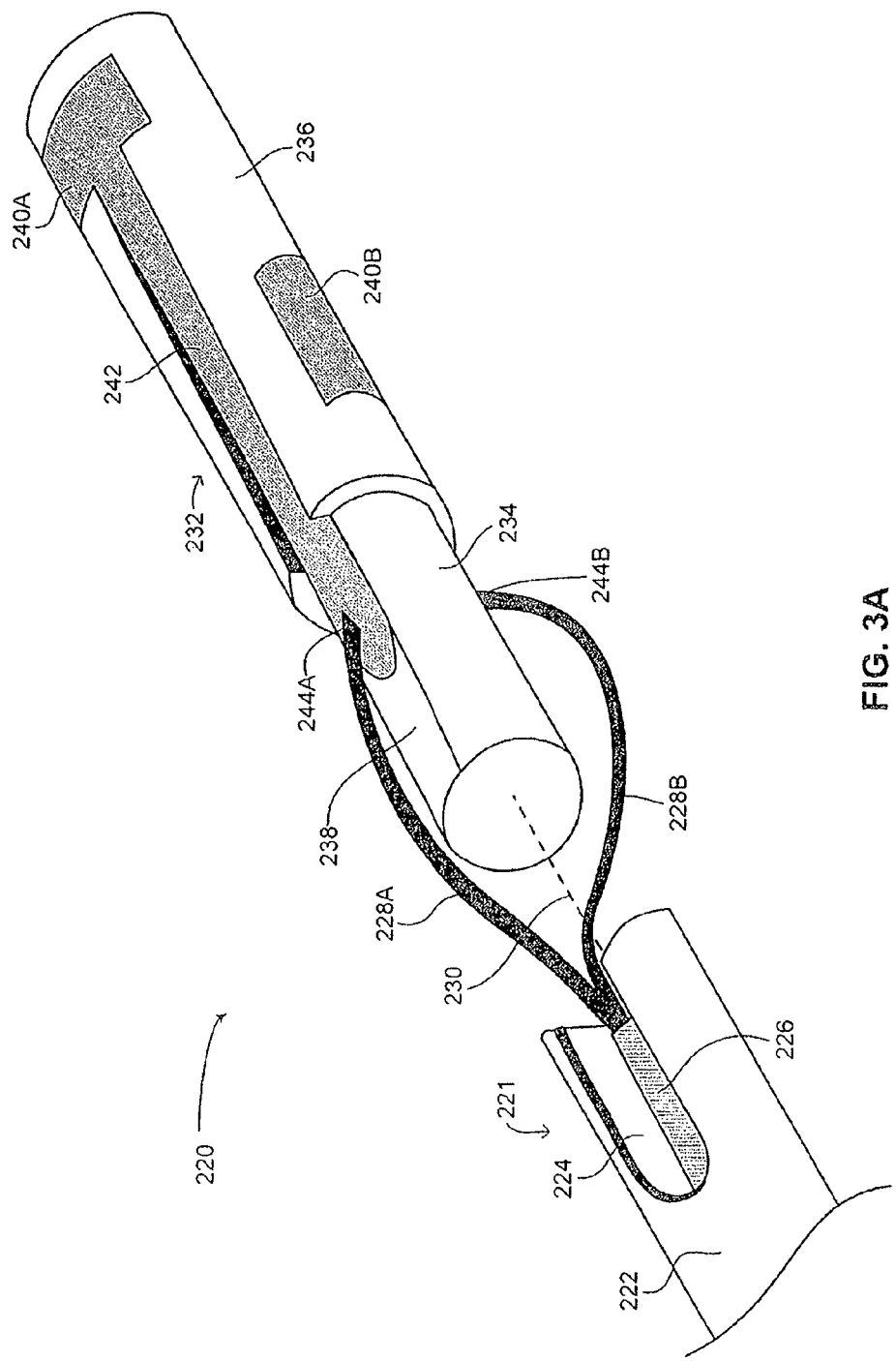
FIG. 3A is a perspective exploded illustration of the guidewire insert of FIG. 2 coupled with a guidewire, constructed and operative in accordance with a further embodiment of the disclosed technique.

Reference is now made to FIG. 3A, which is a perspective exploded illustration of the guidewire insert of FIG. 2 coupled with a guidewire, generally referenced 220, constructed and operative in accordance with a further embodiment of the disclosed technique. As can be seen in FIG. 3A, a guidewire 221 is coupled with a guidewire insert 232. Guidewire 221 includes a hollow walled tube 222 and a lumen (not shown). Inside the lumen, a pair of electrical wires 226 is positioned. Pair of electrical wires 226 includes a first wire 228A and a second wire 228B. The section of guidewire 221 shown is the proximal end of the guidewire. Guidewire 221 also includes, at its proximal end, a first slot 224 and a second slot (not shown in FIG. 3A, shown as a slot 264 in FIG. 3B), both slots being positioned on opposite sides of the proximal end of guidewire 221.

Guidewire insert 232 has a general cylindrical form and includes two sections, a larger diameter section 236 and a smaller diameter section 234. In general, larger diameter section 236 has a diameter which is substantially similar to the diameter of guidewire 221. For example, if guidewire 221 is a guidewire used in a cardiovascular procedure, then the diameter of larger diameter section 236 could be 0.355 millimeters. Smaller diameter section 234 has, in general, a diameter which is substantially similar to the diameter of lumen (not shown) of guidewire 221. In the example above, the diameter of section 234 could be between 0.18 to 0.25 millimeters. As described in FIG. 2, guidewire insert 232 has two conducting rings 240A and 240B. Each conducting ring is coupled with a conducting path. Conducting ring 240A is coupled with conducting path 242. Conducting ring 240B is coupled with a conducting path (not shown in FIG. 3A, shown in FIG. 3B as conducting path 282). As shown in FIG. 3A, smaller diameter section 234 includes a flat surface 238 upon which conducting path 242 is located. A second flat surface, similar to flat surface 238, is, included in smaller diameter section 234, on an opposite side to flat surface 238 (not shown in FIG. 3A, shown in FIG. 3B as flat surface 278). Conducting rings 240A and 240B are substantially similar to, respectively, rings 206A and 206B (both in FIG. 2), and conducting path 242 is substantially similar to both path 208A and path 208A' (both in FIG. 2). First wire 228A is coupled with conducting path 242 at a point 244A. Second wire 228B is coupled with a conducting path (not shown) at a point 244B. The wires can be coupled with the conducting paths by welding, soldering, brazing or bonding with a conductive glue or a conductive bond. As first wire 228A is coupled with conducting path 242, which is coupled with conducting ring 240A, first wire 228A is coupled with conducting ring 240A. As shown in FIG. 3B, second wire 228B is coupled with conducting partial ring 240B.

In general, the diameter of smaller diameter section 234 is substantially similar to the inner diameter of hollow walled tube 222 such that smaller diameter section 234 can be inserted into the lumen of hollow walled tube 222. The diameter of larger diameter section 236 is substantially similar to the outer diameter of hollow walled tube 222 such that when guidewire insert 232 is inserted into guidewire 221, a surface of substantially similar diameter is formed between hollow walled tube 222 and larger diameter section 236. In general, the ratio of lengths between smaller diameter section 234 and larger diameter section 236 is such that a strong coupling is achieved when guidewire insert 232 is inserted into the lumen of guidewire 221. In other words, the length of section 236 is substantially on the same order as the length of section 234. In addition, the coupling of guidewire insert 232 to guidewire 221 can be strengthened by techniques such as press fitting, crimping hollow walled tube 222 over guidewire insert 232, bonding or gluing smaller diameter section 234 to the inner walls of hollow walled tube 222, molding crush ribs onto the surface of smaller diameter section 234 and the like. When guidewire insert 232 is coupled with guidewire 221, guidewire insert 232 is positioned such that flat surface 238, where first wire 228A is coupled to guidewire insert 232, is aligned with first slot 224 and that the other flat surface (not shown), where second wire 228B is coupled to guidewire insert 232, is aligned with the second slot. This is shown by the general positions of guidewire 221 and guidewire insert 232 relative to a dotted centerline 230. Guidewire insert 232 is finally bonded or glued to guidewire 221, and first slot 224 and the second slot are filled using an insulating polymer or an insulating bond, either of which are biocompatible. The insulating polymer or bond is then cured and smoothed, thus forming a biocompatible surface with a diameter substantially similar to the diameter of the proximal section of guidewire 221. It is noted that guidewire insert 232 substantially forms a male coupler section which can be coupled with a female coupler section (not shown) coupled with an external system (not shown).

Reference is now made to FIG. 3B, which is another perspective exploded illustration of the guidewire insert of FIG. 2 coupled with a guidewire, generally referenced 260, constructed and operative in accordance with another embodiment of the disclosed technique. Whereas FIG. 3A showed a guidewire insert and a guidewire from a top perspective view, FIG. 3B shows a guidewire insert and a guidewire from a bottom perspective view. Guidewire 261 includes a hollow walled tube 262 and a lumen (not shown). Inside the lumen, a pair of electrical wires 266 is positioned. Pair of electrical wires 266 includes a first wire 268A and a second wire 268B. The section of guidewire 261 shown is the proximal end of the guidewire. Guidewire 261 also includes, at its proximal end, a second slot 264 and a first slot (not shown in FIG. 3B, shown as a slot 224 in FIG. 3A), both slots being positioned on opposite sides of the proximal end of guidewire 261.

Guidewire insert 272 has a general cylindrical form and includes two sections, a larger diameter section 276 and a smaller diameter section 274. As described in FIG. 2, guidewire insert 272 has two conducting partial rings 280A and 280B. Each conducting partial ring is coupled with a conducting path. Conducting ring 280B is coupled with conducting path 282. Conducting ring 240A is coupled with a conducting path (not shown in FIG. 3B, shown in FIG. 3A as conducting path 242). As shown in FIG. 3B, smaller diameter section 274 includes a flat surface 278 upon which conducting path 282 is located. A second flat surface, similar to flat surface 278, is included in smaller diameter section 274, on an opposite side to flat surface 278 (not shown in FIG. 3B, shown in FIG. 3A as flat surface 238). Conducting rings 280A and 280B are substantially similar to, respectively, rings 206A and 206B (both in FIG. 2), and conducting path 282 is substantially similar to both path 208B and path 208B" (both in FIG. 2). First wire 268A is coupled with conducting path 282 at a point 284A. Second wire 268B is coupled with a conducting path (not shown) at a point 284B. As first wire 268A is coupled with conducting path 282, which is coupled with conducting partial ring 280B, first wire 268A is coupled with conducting partial ring 280B. As shown in FIG. 3A, second wire 268B is coupled with conducting partial ring 280A.

As mentioned above, in general, the diameter of smaller diameter section 274 is substantially similar to the inner diameter of hollow walled tube 262 such that smaller diameter section 274 can be inserted into the lumen of hollow walled tube 262. The diameter of larger diameter section 276 is substantially similar to the outer diameter of hollow walled tube 262 such that when guidewire insert 272 is inserted into guidewire 261, a surface of substantially similar diameter is formed between hollow walled tube 262 and larger diameter section 276. When guidewire insert 272 is coupled with guidewire 261, guidewire insert 272 is positioned such that flat surface 278, where first wire 268A is coupled to guidewire insert 272, is aligned with second slot 264 and that the other flat surface (not shown), where second wire 268B is coupled to guidewire insert 272, is aligned with the first slot. This is shown the general positions of guidewire 261 and guidewire insert 272 relative to a dotted centerline 270.

Figure 3C:
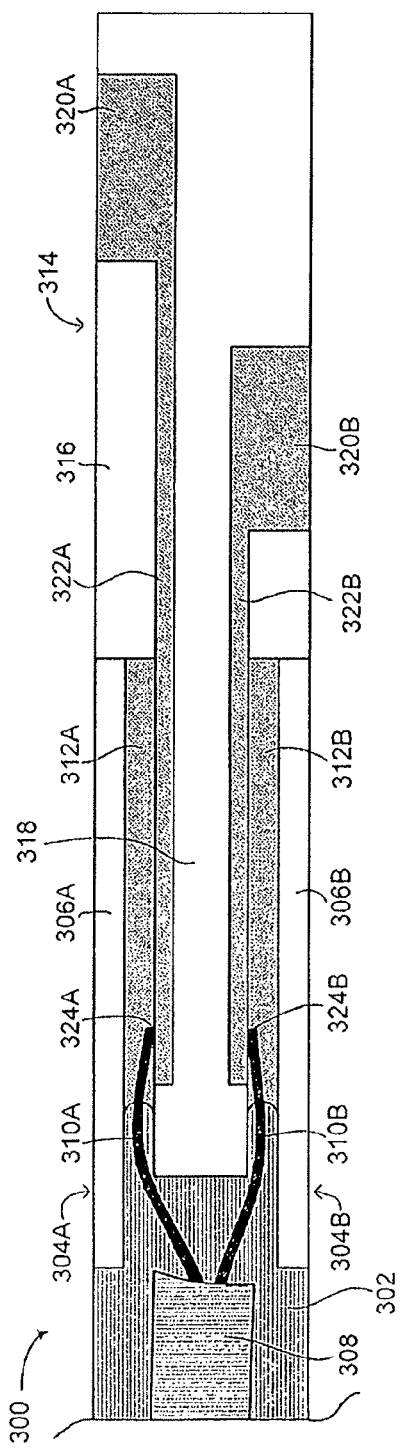
FIG. 3C is a cross-section illustration of the guidewire insert illustrated in FIGS. 3A and 3B, coupled with a guidewire, constructed and operative in accordance with a further embodiment of the disclosed technique.

Reference is now made to FIG. 3C, which is a cross-section illustration of the guidewire insert illustrated in FIGS. 3A and 3B, coupled with a guidewire, generally referenced 300, constructed and operative in accordance with a further embodiment of the disclosed technique. Guidewire 300, which represents the proximal end of the guidewire, includes a hollow walled tube 302, a pair of electrical wires 308, two slots 304A and 304B, a lumen (not shown) and a guidewire insert 314. Slots 304A and 304B run the length of the proximal end of guidewire 300. Pair of electrical wires 308 includes a first wire 310A and a second wire 310B. Guidewire insert 314 includes conducting partial rings 320A and 320B and conducting paths 322A and 322B, with each conducting path being respectively coupled with a single conducting partial ring. Conducting rings 320A and 320B are substantially similar to, respectively, rings 206A and 206B (both in FIG. 2), and conducting paths 322A and 322B are substantially similar to, respectively, paths 208A and 208B (both in FIG. 2). Guidewire insert 314 is formed as described above in FIG. 2, and includes a larger diameter section 316 and a smaller diameter section 318. First wire 310A is coupled with conducting path 322A at a point 324A, and second wire 310B is coupled with conducting path 322B at a point 324B. It is noted that hollow walled tube 302 can serve as a ground contact for electrical elements in the lumen, such as pair of electrical wires 308. Guidewire insert 314 is inserted into the lumen of hollow walled tube 302 and glued or bonded to the inner walls of hollow walled tube 302 as shown in section 312A and 312B. Slots 304A and 304B are filled with an insulating polymer or an insulating bond in sections 306A and 306B. The insulating polymer or bond is cured and smoothed. As can be seen in FIG. 3C, hollow walled tube 302, insulating polymer sections 306A and 306B and larger diameter section 316 together form a smooth surface of substantially the same diameter.

Figure 4A:
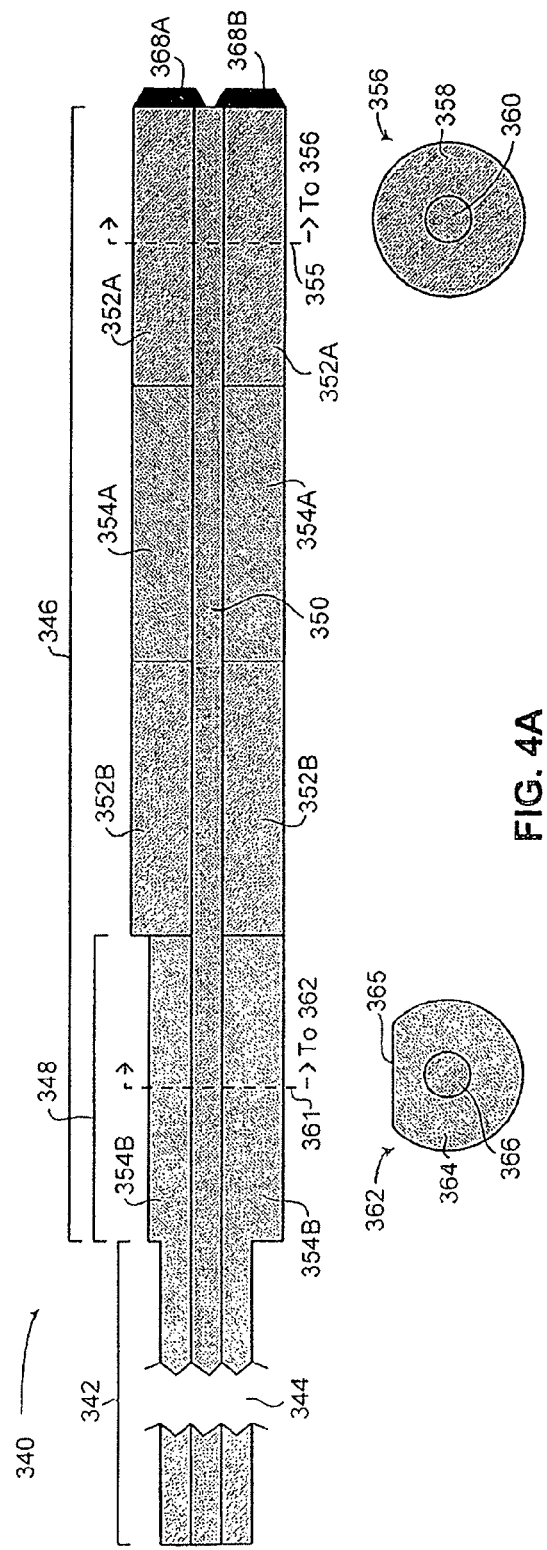
FIG. 4A is a cross-section illustration of another guidewire insert, constructed and operative in accordance with another embodiment of the disclosed technique.

Reference is now made to FIG. 4A, which is a cross-section illustration of another guidewire insert, generally referenced 340, constructed and operative in accordance with another embodiment of the disclosed technique. As described above in FIGS. 2-3C, guidewire insert 340 represents a male coupler section which is coupled with a guidewire (not shown) and can then subsequently be coupled with a female coupler section (not shown) which is coupled with an external system (not shown). Guidewire insert 340 is constructed from a molded polymer and is formed around a central wire 350. Central wire 350 is formed from a conducting metal such as steel, copper, silver, gold, nickel or aluminum and can have a diameter on the order of hundreds of microns, such as 100 microns. The molded polymer is formed around central wire 350. Guidewire insert 340 has a general cylindrical shape, having, a larger diameter section 346 and a smaller diameter section 342. Smaller diameter section 342 may be longer in length than shown in FIG. 4A, as demarcated by a space 344.

In this embodiment, guidewire insert 340 is molded from two different polymer resins by a multiple shot process. One polymer resin is platable by a metal plating technique, while the other is not. In general, both resins are insulating materials. As shown in FIG. 4A, two sections of guidewire insert 340, conducting rings 352A and 352B, are formed from the polymer resin which is platable by a metal plating process and two sections of guidewire insert 340, insulating rings 354A and 354B, are formed from the other polymer resin which is not platable by a metal plating process. Regarding their measurements, conducting rings 352A and 352B can measure, for example, 3-5 millimeters in length, with insulating rings 354A and 354B measuring, for example, 2-3 millimeters in length. Once guidewire insert 340 is molded from the two different resins in the pattern shown in FIG. 4A, an electroplating process is executed on guidewire insert 340. The sections of guidewire insert 340 which were formed from the polymer resin which is platable by a metal plating process are plated whereas the sections formed from the other resin are not. In this respect, conducting rings 352A and 352B are formed and insulating rings 354A and 354B are formed. The metal used in the electroplating process can be, for example, gold, copper, nickel and like. In one embodiment of the disclosed technique, guidewire insert 340 is first plated with a layer of copper, then with a layer of nickel and finally with a layer of gold. In general, the resins and the metal used in the electroplating process are biocompatible. It is noted that conducting rings 352A and 352B are conducting surfaces due to their plating, meaning that just the outer surface of conducting rings 352A and 352B can conduct electrical signals. In this respect, even though central wire 350 is physically coupled with conducting rings 352A and 352B, central wire 350 is not electrically coupled to the conducting rings. In the embodiment shown in FIG. 4A, conducting ring 352A is electrically coupled with central wire 350 by weld beads 368A and 368B which couple the outer plated section of conducting ring 352A to central wire 350. In another embodiment, the outer plated section of conducting ring 352A is coupled to central wire 350 by either a braze bead, a circumferential solder or by a conductive glue.

In guidewire insert 340, in a section 348, insulating ring 354B may be grinded or cut such that its thickness is slightly reduced and a flat surface is formed on one side of insulating ring 354B. In another embodiment, the flat surface formed on one side of insulating ring 354B can be part of the initial mold used to mold guidewire insert 340. A guidewire insert 362 represents a cross-sectional view of insulating ring 354B, as shown by a dotted line 361. Guidewire insert 362 includes a central wire 366, an insulating ring 364 and a flat surface 365. A guidewire insert 356 represents a cross-sectional view of conducting ring 352A, as shown by a dotted line 355. Guidewire insert 356 includes a central wire 360 and a conducting ring 358. As can be seen, guidewire insert 356 has a general cylindrical shape, whereas guidewire insert 362 also has a general cylindrical shape except that on one side, the thickness of the insulating ring has been reduced to form flat surface 365. It is noted that the reduction in thickness of the insulating ring as shown in FIG. 4A represents one embodiment of guidewire insert 340. In another embodiment, insulating ring 354B has the same thickness as insulating ring 354A.

Reference is now made to FIG. 4B, which is a cross-section illustration of the guidewire insert of FIG. 4A, coupled with a guidewire, generally referenced 380, constructed and operative in accordance with a further embodiment of the disclosed technique. A guidewire 382, which represents the proximal end of guidewire 380, includes a hollow walled tube 384, a pair of electrical wires 388, a slot in hollow walled tube 384 shown as a bracket 385, a lumen 386 and a guidewire insert 392. Guidewire 382 can be a hypotube. The slot, as shown by bracket 385, runs the length of the proximal end of guidewire 382. It is noted that unlike the embodiment of the disclosed technique shown in FIGS. 2-3C which includes two slots, guidewire 380 includes only one slot which is located on only one side of hollow walled tube 384. Pair of electrical wires 388 includes a first wire 390A and a second wire 390B. Guidewire insert 314 includes conducting rings 396A and 396B, insulating rings 394A and 394B and central wire 398. Conducting rings 396A and 396B are substantially similar to, respectively, conducting rings 352A and 352B (both in FIG. 4A), and insulating rings 394A and 394B are substantially similar to, respectively, insulating rings 354A and 354B (both in FIG. 4A). Guidewire insert 392 is formed as described above in FIG. 4A, and includes a larger diameter section (not shown) and a smaller diameter section (not shown). Central wire 398 is electrically coupled with conducting ring 396A by weld beads 399A and 399B.

First wire 390A is coupled with central wire 398 at a point 400A, and second wire 390B is coupled with conducting ring 396B at a point 400B. Since conducting ring 396A is coupled with central wire 398 via weld beads 399A and 399B, first wire 390A is coupled with conducting ring 396A. Point 400B is on a surface of conducting ring 396B which is exposed because of the reduced thickness of insulating ring 394B. Both wires are coupled by either being welded, soldered, brazed or bonded using a conductive bonding agent. The reduced thickness in insulating ring 394B enables second wire 390B to be coupled directly to conducting ring 396B without protruding beyond the diameter of guidewire 382. It is noted that hollow walled tube 384 can serve as a ground contact for electrical elements in lumen 386, such as pair of electrical wires 388. In general, the diameter of guidewire 382, shown by an arrow 389, is substantially similar to the diameter of the larger diameter section (not shown) of guidewire insert 392, as shown by an arrow 401. The diameter of lumen 386, as shown by an arrow 387, is substantially similar to the diameter of the smaller diameter section (not shown) of guidewire insert 392, as shown by an arrow 399. In general, the ratio of lengths between the smaller diameter section (not shown) and larger diameter section (not shown) of guidewire insert 392 is such that a strong coupling is achieved when guidewire insert 392 is inserted into lumen 386 of guidewire 382. In addition, the coupling of guidewire insert 392 to guidewire 382 can be strengthened by techniques such as press fitting, crimping hollow walled tube 384 over guidewire insert 392, bonding or gluing the smaller diameter section to the inner walls of hollow walled tube 384, molding crush ribs onto the surface of the smaller diameter section and the like. When guidewire insert 392 is coupled with guidewire 382, guidewire insert 392 is positioned such that the flat surface of insulating ring 394B, above which second wire 390B is positioned, is aligned with slot 385. Guidewire insert 392 is inserted into lumen 386 of hollow walled tube 384 and glued or bonded to the inner walls of hollow walled tube 384. Slot 385 is filled with an insulating polymer or an insulating bond. The insulating polymer or bond is cured and smoothed. As can be seen in FIG. 4B, guidewire 382, insulating polymer 402 and guidewire insert 392 together form a smooth surface of substantially the same diameter. In general, central wire 350 reinforces the connection between guidewire insert 392 and hollow walled tube 384 of the guidewire. Also, central wire 350, as described above, forms a conducting path for one of the wires in pair of electrical wires 388.

Reference is now made to FIG. 5, which is a cross-section illustration of a further guidewire insert, coupled with a guidewire, generally referenced 420, constructed and operative in accordance with another embodiment of the disclosed technique. As described above in FIGS. 2-4B, guidewire insert 434 represents a male coupler section which is coupled with a guidewire 422 and can then subsequently be coupled with a female coupler section (not shown) which is coupled with an external system (not shown). Guidewire 422, which represents the proximal end of guidewire 420, includes a hollow walled tube 424, a pair of electrical wires 428, a slot in hollow walled tube 424 shown as a bracket 432, a lumen 426 and a guidewire insert 434. Guidewire 422 can be a hypotube. The slot, as shown by bracket 432, runs the length of the proximal end of guidewire 420. It is noted that unlike the embodiment of the disclosed technique shown in FIGS. 2-3C which includes two slots, guidewire 420 includes only one slot which is located on only one side of hollow walled tube 424. Pair of electrical wires 428 includes a first wire 430A and a second wire 430B. Guidewire insert 434 includes a first conducting layer 442, a first insulating layer 440, a second conducting layer 438 and a second insulating layer 436.

In one embodiment, guidewire insert 434 is formed from a molded polymer or from a micromolded plastic. First conducting layer 442 is formed by coating or plating guidewire insert 434 with a conductive material, such as gold, copper, nickel and the like. As mentioned above, in one embodiment, a layer of copper, is first plated, followed by a layer of nickel and finally a layer of gold. First conducting layer 442 is partially covered, as shown in FIG. 5, by first insulating layer 440. Second conducting layer 438 is formed by partially coating or plating first insulating layer 440 with a conductive material as shown in FIG. 5. Second conducting layer 438 is partially covered by second insulating layer 436, as shown in FIG. 5. First and second insulating layers 440 and 436 can be thin walled heat shrink tubing such as thin walled polyester (PET) heat shrink tubing, sprayed polymers, dipped polymers, ceramic coatings such as alumina and the like. In another embodiment, guidewire insert 434 is formed from a conductive metal by a process of either micro-machining, grinding or drawing. In this embodiment, first conducting layer 442, which in the first embodiment was plated or coated onto the molded polymer forming the guidewire insert, is the conductive metal itself, upon which a first insulating layer is positioned. This embodiment is cost effective as the cost of plating first conducting layer 442 is saved. Also, this embodiment enables a stiffer and more robust guidewire insert to be formed as the guidewire insert is formed from a metal and not from a polymer or plastic.

First wire 430A is coupled with first conducting layer 442 at a point 446A, and second wire 430B is coupled with second conducting layer 438 at a point 446B. It is noted that hollow walled tube 424 can serve as a ground contact for electrical elements in lumen 426, such as pair of electrical wires 428. It is also noted that both of points 446A and 446B, where first wire 430A and second wire 430B are respectively coupled with guidewire insert 434, are located on the side of guidewire 422 where the slot, as shown by bracket 432, is located. This enables one side of guidewire insert 434 to be coupled directly with one side of guidewire 422 by a bond or a glue, as described below. In general, the diameter of guidewire 422, shown by an arrow 452, is substantially similar to the diameter of the larger diameter section (not shown) of guidewire insert 434, as shown by an arrow 450. The diameter of lumen 426, as shown by an arrow 454, is substantially similar to the diameter of the smaller diameter section (not shown) of guidewire insert 434, as shown by an arrow 448. In general, the ratio of lengths between the smaller diameter section (not shown) and larger diameter section (not shown) of guidewire insert 434 is such that a strong coupling is achieved when guidewire insert 434 is inserted into lumen 426 of guidewire 422. In addition, the coupling of guidewire insert 434 to guidewire 422 can be strengthened by techniques such as press fitting, crimping hollow walled tube 424 over guidewire insert 434, bonding or gluing the smaller diameter section to the inner walls of hollow walled tube 424, molding crush ribs onto the surface of the smaller diameter section and the like. Guidewire insert 434 is inserted into lumen 426 of hollow walled tube 424 and glued or bonded to the inner walls of hollow walled tube 424 using a non-conductive polymer bond 444. Slot 432 is filled with non-conductive polymer bond 444, which can also be an insulating polymer or an insulating bond. The insulating polymer or bond is cured and smoothed. As can be seen in FIG. 5, guidewire 422, insulating polymer 444 and guidewire insert 434 together form a smooth surface of substantially the same diameter.

The male coupler described above in FIGS. 1B, 3A, 3B, 3C, 4A, 4B and 5 is coupled with, or is integrated with, as in the case of FIG. 1B, a guidewire. It is noted that the male coupler described in the above mentioned figures can also be coupled with, or integrated with, other invasive apparatuses such as stylets having electrical leads and various types of catheters, such as catheters bearing balloons and stents at their distal ends. In integrating, or coupling, the male coupler of the disclosed technique with the other invasive apparatuses mentioned above, the electrical elements of such apparatuses, such as electrical leads, would be coupled with the male coupler as described above regarding electrical wires, such as first wire 228A and second wire 228B (both in FIG. 3A).

The guidewire of the disclosed technique, as mentioned above, couples with an external system, which is usually positioned in a treatment area. In this case, a user of the disclosed technique, such as a physician, inserts the male coupler, which, as mentioned above, is coupled with the guidewire, to a female coupler. The female coupler couples the male coupler, and thus the guidewire, with the external system. The female coupler, according to the disclosed technique, is divided into two parts which are a disposable part and a fixed part, with the disposable part inserted into the fixed part. The disposable part and the fixed part are mechanically and electrically coupled there between, as explained below. In general, the fixed part is coupled with the external system in the treatment area and the disposable part is coupled with the male coupler of the guidewire.

Reference is now made to FIGS. 6A and 6B, which are schematic perspective illustrations of the guidewire male coupler, generally referenced 455, constructed and operative in accordance with a further embodiment of the disclosed technique. FIG. 6A illustrates a perspective exploded illustration of male coupler 455. Male coupler 455 includes three tubular segments, segment 456, segment 457 and segment 458. Tubular segment 456 includes two reduced diameter sections delineated by a bracket 461 and by a bracket 463 and a regular section delineated by a bracket 462 there between. Tubular segment 457 includes a slit 459. Tubular segment 458 includes slit 460, a reduced diameter section delineated by a bracket 464 and a regular section delineated by a bracket 465. In FIG. 6A segments 456, 457 and 458 of guidewire insert are illustrated separately.

The outer diameter of reduced diameter section 461 is slightly less then the inner diameter of a guidewire (not shown). The outer diameters of regular sections 462 and 465 are substantially similar to the outer diameter the guidewire. The outer diameter of reduced diameters sections 463 and 464 are slightly less then the inner diameter of tubular segment 457. The outer diameter of tubular segment 457 is substantially similar to the outer diameter of the guidewire.

Tubular segments 456, 457 and 458 are made of a conducting metal (e.g., Nirosta stainless steel, Nitinol). Tubular segment 456 is partially of fully coated with an electrical insulating material (e.g., insulating glue, insulating polymer, Alumina) such that tubular segment 456 does not form an electrical contact with neither the guidewire nor with tubular segments 457 and 458. Alternatively, tubular segment 456 may be made of an insulating material (e.g., polymer, Ceramic). Tubular segment 458 is partially coated with an electrical insulating material. Reduced diameter section 464 is fully coated with an electrical insulating material while regular section 465 may be partially coated. Thus, tubular segment 458 does not form an electrical contact with tubular segments 457 and 456. In FIG. 6A segments 456, 457 and 458 of male coupler 455 are illustrated separately.

FIG. 6B illustrates a perspective schematic illustration of male coupler 455 assembled. Reduced diameter section 461 is inserted in the guidewire (not shown). Reduced diameter section 463 (FIG. 6A—not shown in FIG. 6B) is inserted into one side tubular segment 457. Reduced diameter section 464 (FIG. 6A—not shown in FIG. 6B) is inserted into the other side of tubular segment 457. Since tubular sections 457 and 458 are made of conducting metal, and do not form an electrical contact there between tubular sections 457 and 458 form two conducting rings. These conducting rings are coupled with a twisted pair of wires (no shown), exiting through slits 459 and 460. The twisted pair lead to and are coupled with a sensor (also not shown), placed along the length of the guidewire. Thus the sensor may be coupled with an external device via the conducting rings and a female coupler (not shown).

Figure 6C:
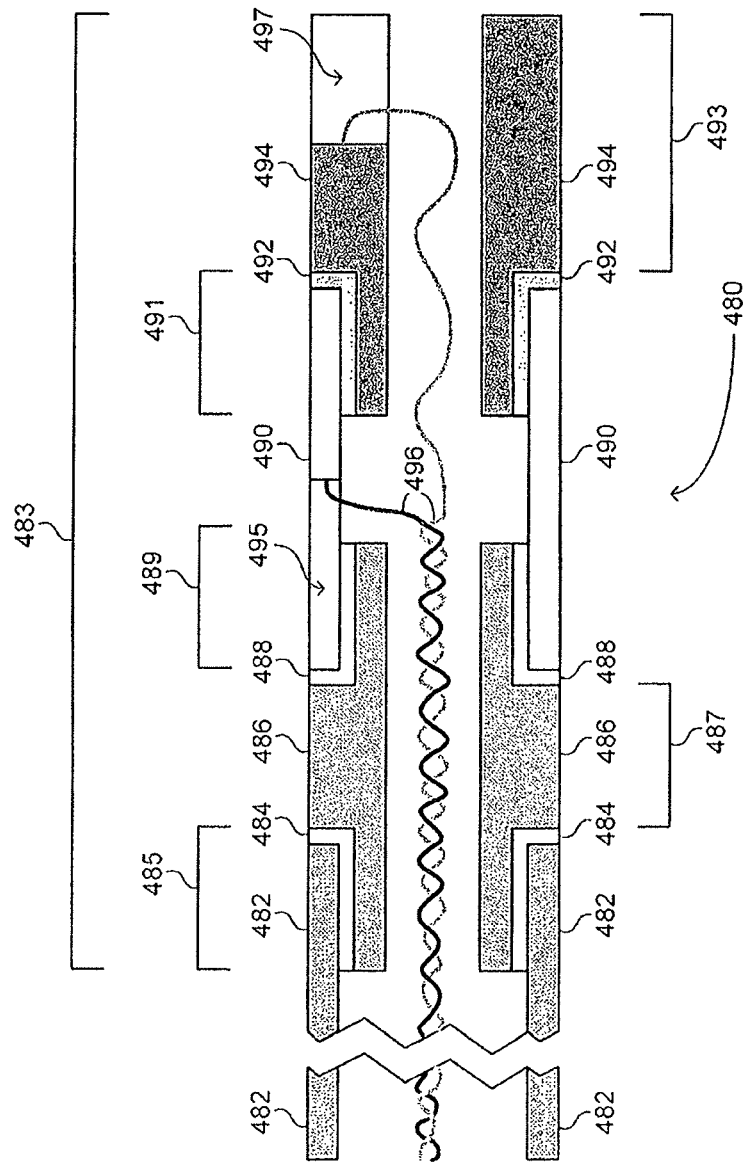
FIG. 6C, is a schematic cross-section illustration of a guidewire male coupler, along a plane parallel to the length of the male coupler, constructed and operative in accordance with another embodiment of the disclosed technique.

Reference is now made to FIG. 6C, which is a schematic cross-section illustration of a guidewire male coupler, generally reference 480, along a plane parallel to the length of male coupler 480, constructed and operative in accordance with another embodiment of the disclosed technique. In FIG. 6C, male coupler 480 is assembled and inserted into a guidewire 482. Guidewire 482 includes a hollow tube. The length of male coupler 480 is delineated by a bracket 483. Male coupler 480 includes three tubular segments, tubular segment 486, tubular segment 490 and tubular segment 494.

Tubular segment 486 includes two reduced diameter sections delineated by bracket 485 and 489, and a regular section delineated by a bracket 487 between the reduced diameter sections 484 and 489. Tubular segment 490 includes a slit 495. Tubular segment 494 includes slit 497, a reduced diameter section delineated by bracket 491 and a regular section delineated by bracket 493.

The outer diameter of reduced diameter section 485 is slightly smaller than the inner diameter of the hollow tube of guidewire 482. The outer diameters of regular sections 493 and 497 are substantially similar to the outer diameter the hollow tube of guidewire 482. The outer diameter of reduced diameters sections 489 and 491 are slightly small then the inner diameter of tubular segment 490. The outer diameter of tubular segment 490 is substantially similar to the outer diameter of the hollow tube of guidewire.

Tubular segments 486, 490 and 494 are made of a conducting metal (e.g., Nirosta stainless steel, Nitinol). Alternatively, tubular segment 486 may be made of an insulating material (e.g., polymer, ceramic). Reduced diameter section 485 of tubular segment 486 is coated with an insulating layer 484 made of an insulating material (e.g., insulating glue, insulating polymer, Alumina). Reduced diameter section 485 of tubular segment 486 is inserted into the hollow tube of guidewire 482. Tubular segment 486 and guidewire 482 do not form an electrical contact there between due to insulating layer 484. Reduced diameter section 489 of tubular segment 486 is coated with an insulating layer 488. Reduced diameter section 489 of tubular segment 486 is inserted into one side of tubular segment 490. Tubular segment 486 and tubular segment 490 do not form an electrical contact there between due to insulating layer 488. Reduced diameter section 491 of tubular segment 494 is coated with an insulating layer 492. Reduced diameter section 491 of tubular segment 494 is inserted into the other side of tubular segment 490. Tubular segment 494 and tubular segment 490 do not form an electrical contact there between due to insulating layer 492. Thus, tubular segment 494 and tubular segments 490 form two conducting rings. These conducting rings are coupled with a twisted pair of wires 496. One of the wires of twisted pair 496 exits through slit 495 and is coupled with tubular segment 490

(e.g., by welding, soldering, bonding or gluing with conducting glue). The other wire of twisted pair 496 exists through slit 497 and is coupled with tubular segment. Thus, sensor, placed along the length of guidewire 482 may be coupled with an external device via the conducting rings and a female coupler (not shown).

It is noted that the order of insertion of tubular segments 486, 490 and 494 into the hollow tube of guide wire 482 may be changed. For example, tubular section 494 is inserted into the hollow tube of guidewire 482. Reduced diameter section 468 of tubular segment 486 is inserted into regular section 493 of tubular segment 494. Reduced diameter section 489 of tubular segment 486 is inserted into tubular segment 490. According to a further embodiment of the disclosed technique, tubular segments 490 and 486 may be replaced with a tubular segment similar to tubular segment 494. Accordingly reduced diameter section 491 of tubular segment 494 is inserted into the hollow tube of guidewire 482 and the reduced diameter of the tubular segment similar to tubular segment 494 is inserted into regular section 493 of tubular segment 494.

Figures 7A, 7B:
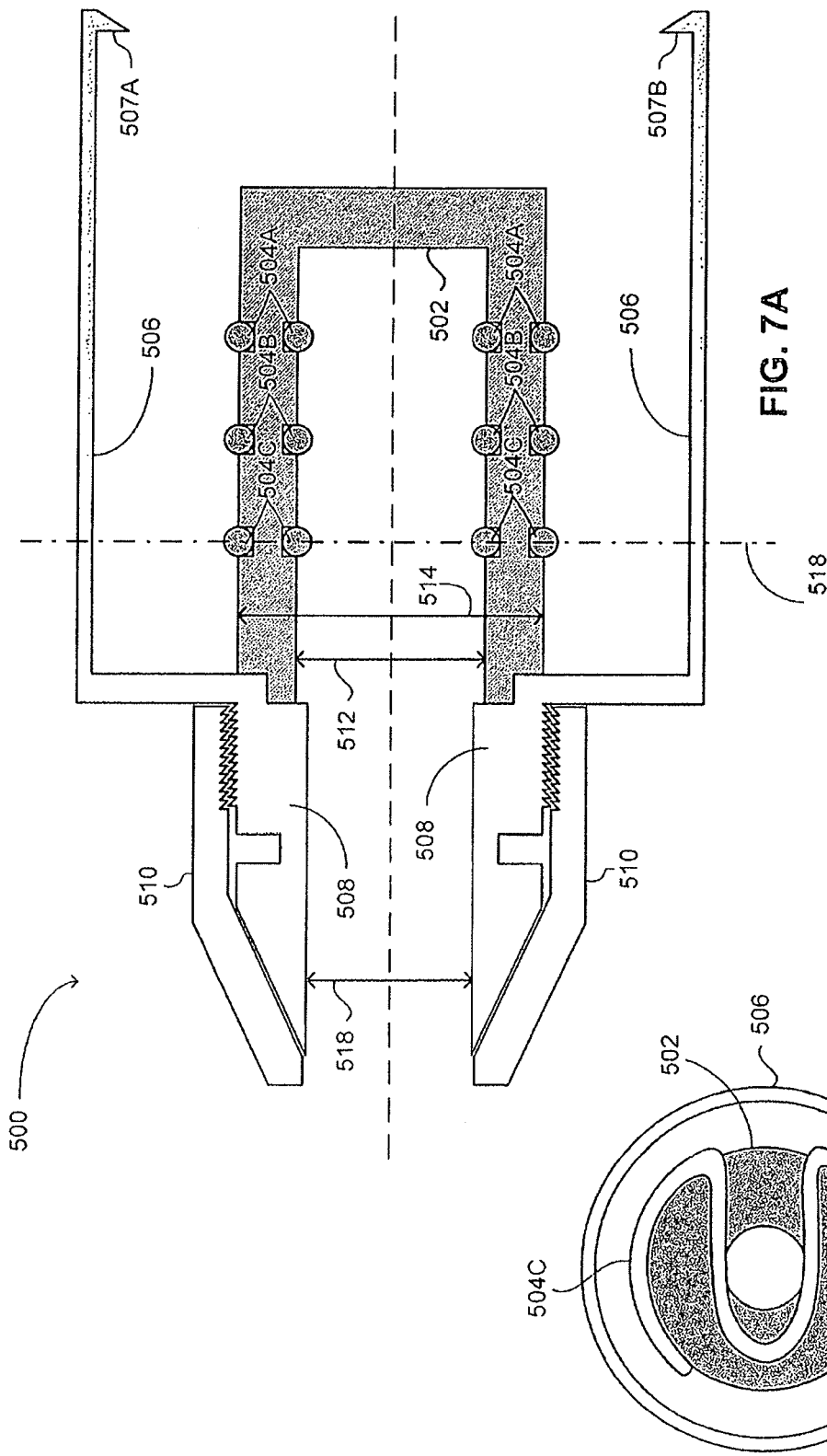
FIGS. 7A and 7B are illustrations of cross-sectional views of a disposable part in a female coupler, constructed and operative in accordance with another embodiment of the disclosed technique.

Reference is now made to FIGS. 7A and 7B, which are illustrations of cross-sectional views of a disposable part, generally referenced 500, in a female coupler, constructed and operative in accordance with another embodiment of the disclosed technique. FIG. 7A is a longitudinal cross-section of disposable part 500. Disposable part 500 includes a disposable tubular body 502, conducting springs 504A, 504B and 504C, a sheath 506, a collet chunk 508 and a collet cup 510. Tubular body 502 is essentially in the shape of a tube with an open end and a closed end, having an inner diameter 512 and an outer diameter 514. Sheath 506 further includes two locking juts 507A and 507B. The purpose of locking juts 507A and 507B is explained below in conjunction with FIGS. 9A and 9B. Inner diameter 512 of disposable tubular body 502 is slightly larger than the outer diameter of the male connector (e.g., the male coupler of FIG. 4B). Inner diameter 512 is on the order of hundreds of micrometers (e.g., 355 micrometers).

Conducting springs 504A, 504B and 504C are coupled with disposable tubular body 502 such that each spring has a portion thereof in contact with the inner wall of disposable tubular body 502 and a portion in contact with the outer wall of disposable tubular body 502. Collet chunk 508 is coupled with disposable tubular body 502 at the open end of tubular body 502. Sheath 506 is coupled with disposable tubular body 502 at the open end of disposable tubular body 502 and extends toward the closed end of disposable tubular body 502. Locking juts 507A and 507B are located at the end of sheath 506 that extends toward the closed end of disposable tubular body 502. FIG. 7B is a lateral cross-section of disposable part 500 at dash-dot line 518 (FIG. 5A). The shape of the lateral cross-section of conducting spring 504C represents an exemplary embodiment thereof. The lateral cross-section of conduction spring 504C may exhibit other shapes such as the shape of the letter S, or the shape of two C's one on top of the other. It is noted that typically conducting springs 504A and 504B are similar to conducting spring 504C.

As mentioned above, collet chunk 508 is coupled with disposable tubular body 502. Collet chunk 508 has an inner diameter substantially similar to that of the male connector. For example, diameter 518 is in the order of hundreds of micrometers (e.g., 350 micrometers). The purpose collet chunk 508 is to secure the guidewire in place and prevent longitudinal and torsional slip of the guidewire. When collet cup 510 is screwed onto collet chunk 508, collet cup 510 exerts a longitudinal force on collet chunk 508. Collet chunk 508 transforms this longitudinal force to a centripetal force.

Figure 8A:
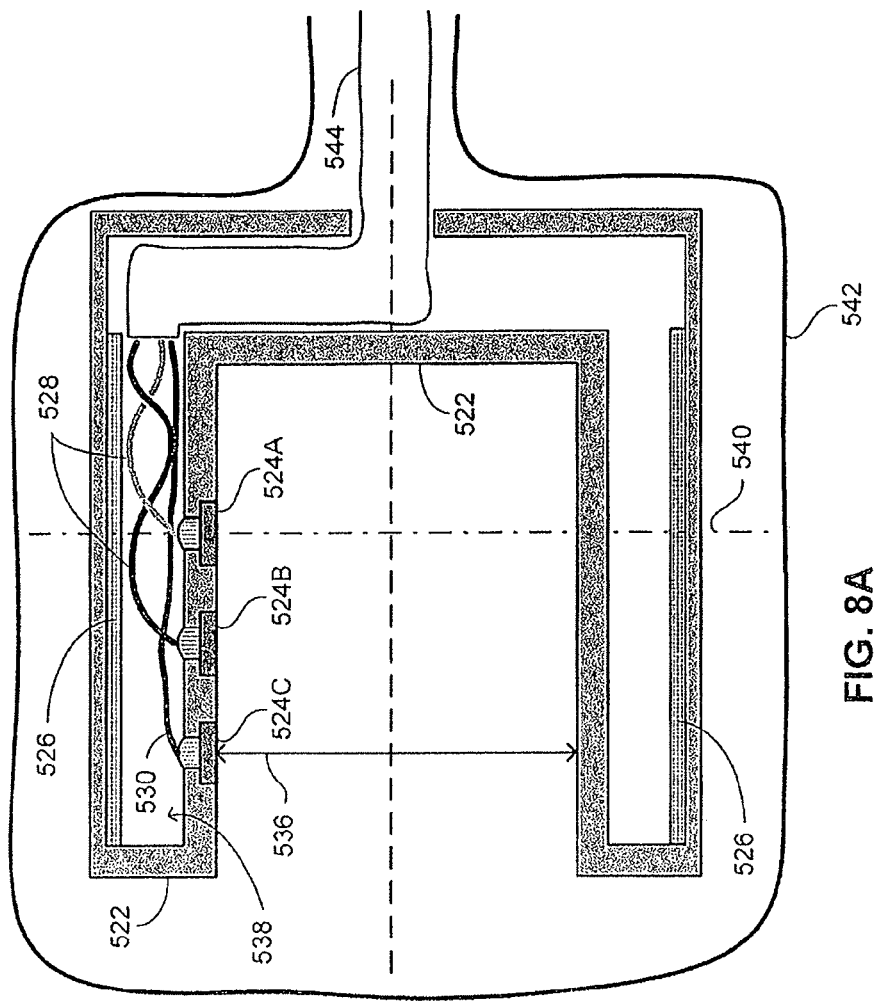
FIGS. 8A and 8B are illustrations of cross-sectional views of a non-disposable part in a female coupler, constructed and operative in accordance with a further embodiment of the disclosed technique.
Figure 8B:
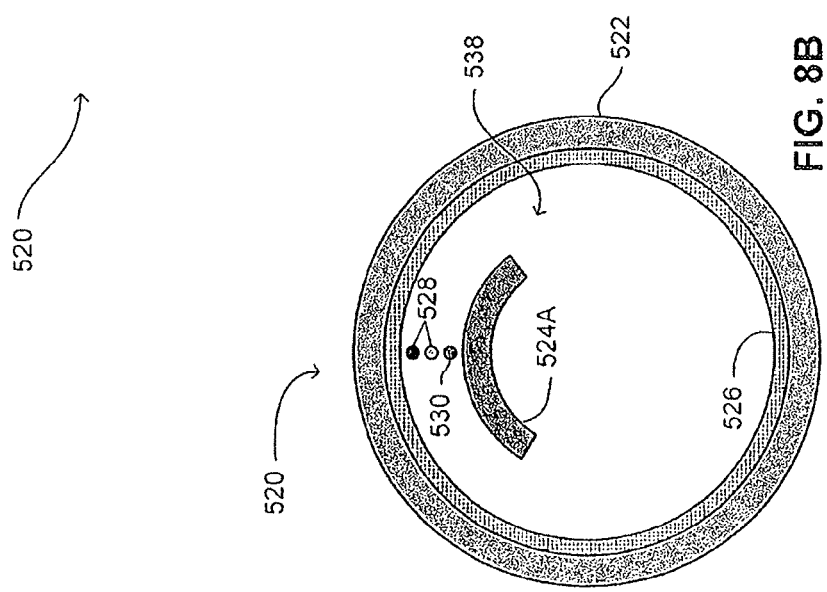

Reference is now made to FIGS. 8A and 8B which are illustrations of cross-sectional views of a non-disposable part, generally referenced 520, in a female coupler, constructed and operative in accordance with a further embodiment of the disclosed technique. Non-disposable part 520 includes a non-disposable tubular body 522, contacts 524A, 524B and 524C, a shielding tube 526, a twisted pair of wires 528 referred to herein as twisted pair 528, a ground wire 530, a wiring sheath 544 and a sterile sleeve 542. Non-disposable tubular body 522 includes a cavity 538 between the inner and outer walls thereof.

Contacts 524A, 524B and 524C are coupled with non-disposable tubular body 522. Shielding tube 526 is also coupled with non-disposable tubular body 522. Twisted pair 528 is coupled with contacts 524A and 524B (e.g., by welding or bonding). Ground wire 530 is coupled with contact 524C (e.g., by welding or bonding). Twisted pair 528 and ground wire 530 are inserted into wiring sheath 544. Non-disposable part 520, with the majority of wiring sheath 544, is draped in a sterile sleeve 542. Sterile sleeve 542 has an opening ripped therein (not shown), at the open end of non-disposable tubular body 522 (e.g., as two slits exhibiting the shape of a cross).

The circumference of contacts 524A, 524B and 524C exhibits the shape of an arc with a subtending angle on the order of at most tens of degrees. The inner face of each of contacts 524A, 524B and 524C faces into non-disposable tubular body 522 and the outer face of each of contacts 524A, 524B and 524C faces cavity 538. Contacts 524A, 524B and 524C encircles a portion of the inner wall of tubular body 522 relative to the subtending angle of contacts 524A, 524B and 524C. The shape of the longitudinal cross-section of contacts 524A, 524B and 524C is that of a rectangle. It is noted that this shape is an exemplary embodiment. The longitudinal cross-section of contacts 524A, 524B and 524C may exhibit other shapes such as the shape of the letter S and the shape of the letter C. In general, the shape of contacts 524A, 524B and 524C should create a spring force on conducting springs 504A, 504B and 504C (FIG. 7A).

The inner diameter of contacts 524A, 524B and 524C and of non-disposable tubular body 522 is on the order of millimeters (e.g., typically between five to six millimeters) such that a disposable part, such as disposable part 500, fits into non-disposable tubular body 522. Twisted pair 528 and ground wire 530 pass within cavity 538. Shielding tube 526 is coupled with non-disposable tubular body 522 such that shielding tube 526 shields twisted pair 528 and ground wire 530 in cavity 538 from electromagnetic interferences. Shielding tube 526 is typically made of a ferromagnetic material (e.g. a μ-metal or nickel-iron). FIG. 8B is a lateral cross-section of non-disposable part 520 at dash-dot line 540 (FIG. 8A)

Figure 9:
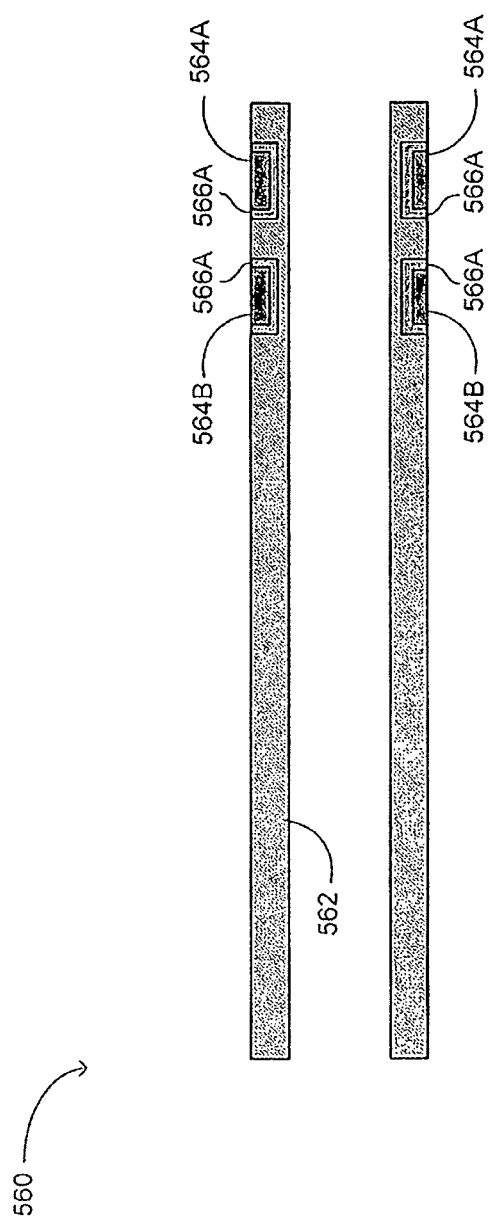
FIG. 9 is an illustration of a cross-sectional view of a male coupler, constructed and operative in accordance with another embodiment of the disclosed technique.

Reference is now made to FIG. 9 which is an illustration of a cross-sectional view of a male coupler, generally referenced 560, constructed and operative in accordance with another embodiment of the disclosed technique. Male connector 560 includes a tube 562, two male conducting rings 564A and 564B and two respective insulating layers 566A and 566B. Male conducting rings 564A and 564B are coupled with tube 562 via insulating layers 566A and 566B respectively. It is noted that male connector 560 may be any one of the male couplers described hereinabove in conjunction with FIGS. 1B, 3A, 3B, 3C, 4A, 4B, 5, 6A, 6B and 6C.

Figure 10A:
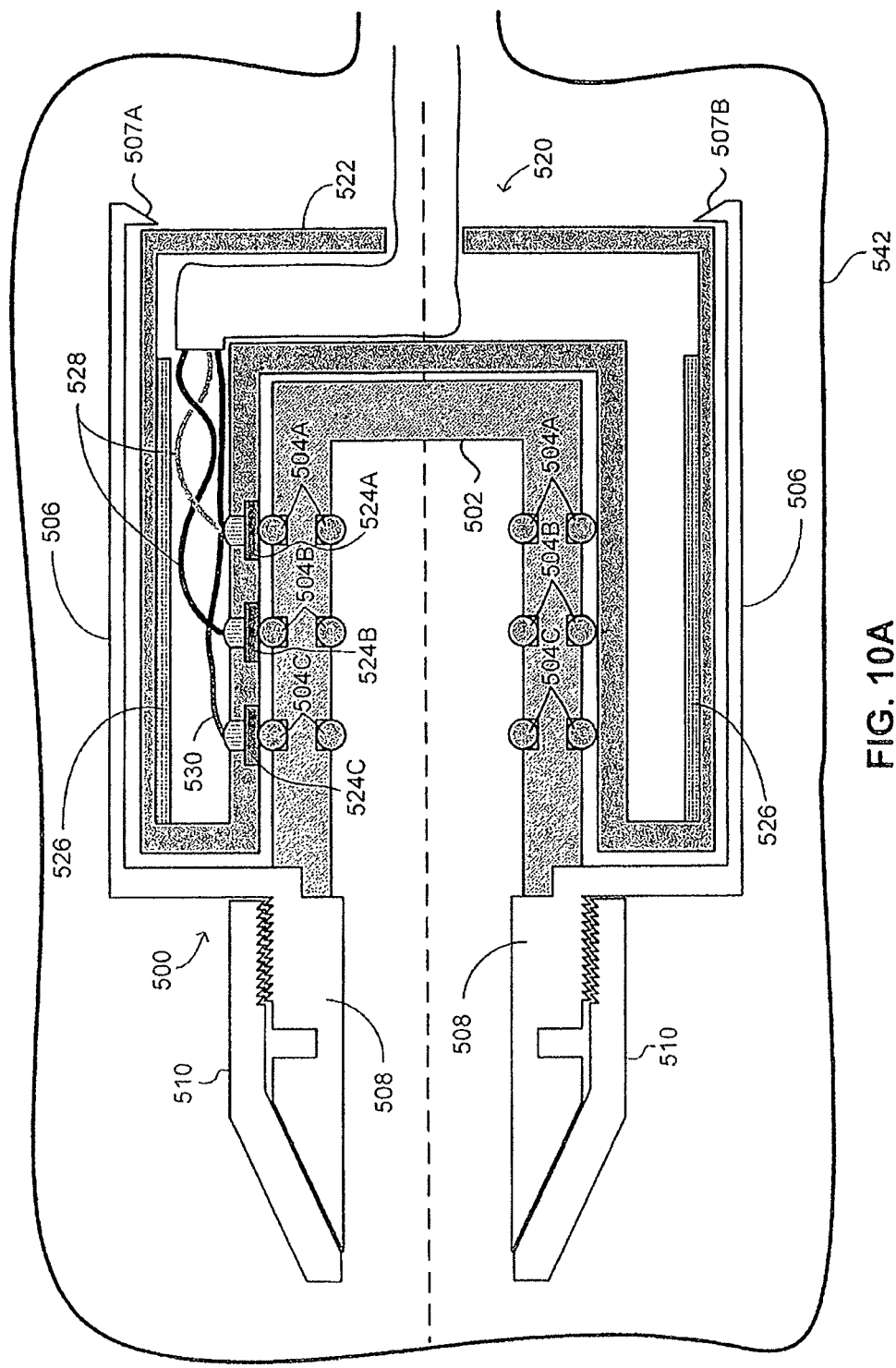
FIG. 10A is an illustration of a cross-sectional view of the disposable part of FIG. 6A inserted into the non-disposable part of FIG. 8A, constructed and operative in accordance with a further embodiment of the disclosed technique.
Figure 10B:
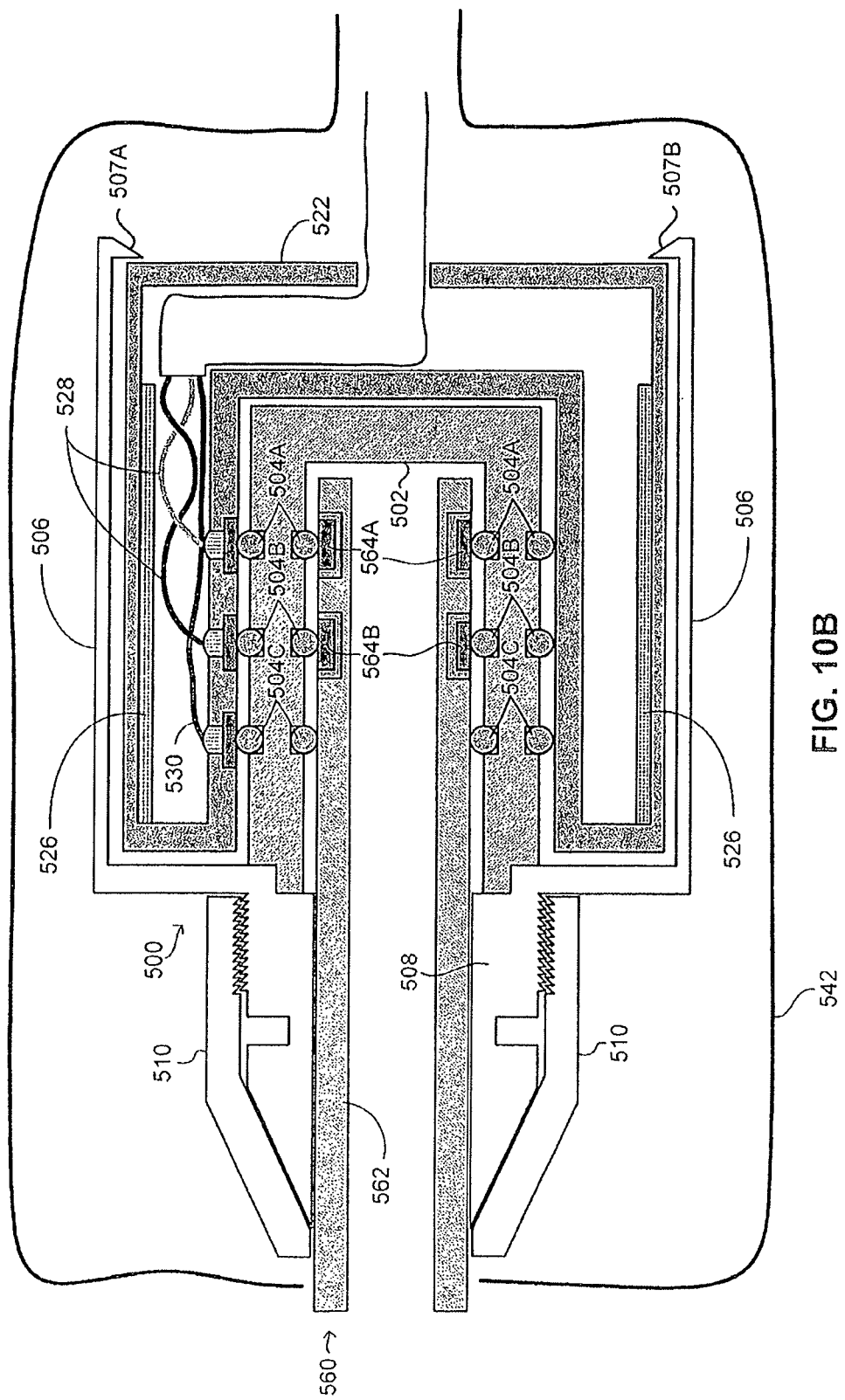
FIG. 10B is an illustration of a cross-sectional view of the disposable part of FIG. 7A inserted into the non-disposable part of FIG. 8A and the male coupler of FIG. 8 inserted into the disposable part of FIG. 7A, constructed and operative in accordance with a further embodiment of the disclosed technique.

Reference is now made to FIGS. 10A and 10B. FIG. 10A is an illustration of a cross-sectional view of the disposable part of FIG. 7A inserted into the non-disposable part of FIG. 8A, constructed and operative in accordance with a further embodiment of the disclosed technique. Disposable part 500 is inserted into non-disposable part 520 through the opening in sterile sleeve 542. When disposable part 500 is inserted into non-disposable part 520, sheath 506 slides over body 522 of non-disposable part 520. Once disposable part 500 is fully inserted into non-disposable part 520, locking juts 507A and 507B slide over the end of non-disposable tubular body 522, thus locking disposable part 500 in non-disposable part 520. When disposable part 500 is locked into non-disposable part 520, conducting springs 504A, 504B and 504C are in electrical contact with contacts 524A, 524B and 524C respectively.

FIG. 10B is an illustration of a cross-sectional view of the disposable part of FIG. 7A inserted into the non-disposable part of FIG. 8A and the male coupler of FIG. 9 inserted into the disposable part of FIG. 7A, constructed and operative in accordance with a further embodiment of the disclosed technique. Male connector 560 is inserted into disposable part 500 through the opening in sterile sleeve 542. Thus both male and female connectors are covered with sterile sleeve 542 allowing an operator to touch the male and female connectors with a substantially reduced risk of contamination. Male connector 560 is inserted into the open end of disposable tubular body 502. Once male connector 560 is fully inserted into the open end disposable tubular body 502, male conducting rings 564A and 564B are in electrical contact with conducting springs 504A and 504B. Conducting spring 504C is in electrical contact with the body of tube 562. Thus, male conducting rings 564A and 564B are electrically coupled with twisted pair 528 and tube 562 is electrically coupled with ground wire 530. When male connector 560 is fully inserted into disposable tubular body 502, collet cup 510 is screwed onto collet chunk 508 and exerts a longitudinal force on collet chunk 508. Collet chunk 508 transforms this longitudinal force to a centripetal force thus securing the male connector in place and preventing longitudinal and torsional slip of the guidewire.

Figure 11:
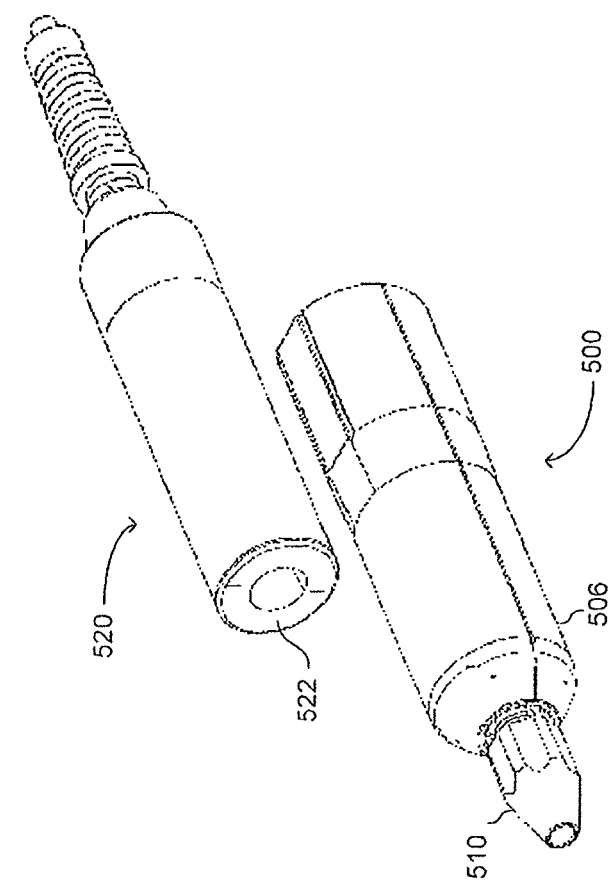
FIG. 11 is an isometric perspective illustration of a disposable part and a non-disposable part of a female coupler, constructed and operative in accordance with another embodiment of the disclosed technique.

Reference is now made to FIG. 11, which is an isometric perspective illustration of a disposable part and a non-disposable part of a female coupler, constructed and operative in accordance with another embodiment of the disclosed technique. Collet cup 510 and sheath 506 of disposable part 500 and disposable tubular body 522 of non-disposable part 520 are seen.

It will be appreciated by persons skilled in the art that the disclosed technique is not limited to what has been particularly shown and described hereinabove. Rather the scope of the disclosed technique is defined only by the claims, which follow.

The invention claimed is:

1. A male coupler for a guidewire, the male coupler comprising:
    a connector section physically coupled with the guidewire, said connector section comprising a first portion having a first outer diameter, a second portion having a second outer diameter that is smaller than said first outer diameter, and a transition portion disposed between said first portion and said second portion and having an outer diameter that tapers from said first outer diameter to said second outer diameter;
    at least one conducting ring having a third outer diameter that is equal to said first outer diameter and disposed proximal of said first portion of said connector section; and
    adhesive coupling said connector section with said at least one conducting ring.

2. The male coupler of claim 1, wherein said first portion is distal of said second portion.

3. The male coupler of claim 1, comprising at least two conducting rings, both of said at least two conducting rings having the third outer diameter.

4. The male coupler of claim 3, wherein a longitudinal axis extends through said conducting rings and said connector section, the male coupler further comprising a polymer disposed axially between said two conducting rings.

5. The male coupler of claim 3, wherein a polymer that is different from said adhesive is disposed between said connector section and at least one of said conducting rings.

6. The male coupler of claim 1, wherein said adhesive is a first adhesive, further comprising a second adhesive at a proximal-most portion of said male coupler.

7. The male coupler of claim 6, wherein said first adhesive is contiguous with said second adhesive.

8. The male coupler of claim 1, further comprising at least one electrical wire that is electrically coupled with said at least one conducting ring with an electrically-conductive adhesive.

9. A male coupler for an elongate medical device, the male coupler comprising:
    a first layer, the first layer comprising a first portion having a first outer diameter, a second portion having a second outer diameter that is smaller than said first outer diameter, and a transition portion disposed between said first portion and said second portion and having an outer diameter that tapers from said first outer diameter to said second outer diameter;
    a second layer comprising polymer, said second layer comprising a portion having a third outer diameter that is smaller than said first outer diameter;
    a third layer comprising polymer, wherein said first layer, said second layer, and said third layer are all arranged around a longitudinal axis; and
    a lumen extending through said first layer, said second layer, and said polymer layer, parallel with said longitudinal axis;
    wherein said first layer, said second layer, and said third layer at least partially axially overlap.

10. The male coupler of claim 9, further comprising at least one wire extending through said lumen.

11. The male coupler of claim 9, wherein said second layer and said third layer at least partially overlap said transition portion of said first layer.

12. The male coupler of claim 9, wherein said second layer comprises a transition region that tapers from said third outer diameter to a fourth outer diameter.

13. The male coupler of claim 12, wherein a proximal-most portion of said second layer is proximal of a proximal-most portion of said third layer.

* * * * *